United States Patent [19]

Curtze et al.

[11] Patent Number: 4,910,200
[45] Date of Patent: Mar. 20, 1990

[54] ACRYLIC ACID MORPHOLIDES, FUNGICIDAL COMPOSITIONS AND USE

[75] Inventors: Jurgen Curtze, Geisenheim-Johannisberg; Helmut Pieper; Josef Nickl, both of Biberach an der Riss; Heinz-Manfred Becher, Bingen am Rhein; Guido Albert, Hackenheim; Christo Drandarevski, Ingelheim am Rhein; Sigmund Lust, Darmstadt; Ludwig Schroder, Ingelheim am Rhein, all of Fed. Rep. of Germany

[73] Assignee: Celamerck GmbH & Co. KG, Fed. Rep. of Germany

[21] Appl. No.: 917,022

[22] Filed: Oct. 9, 1986

[30] Foreign Application Priority Data

Oct. 9, 1985 [DE] Fed. Rep. of Germany ....... 3536029
Nov. 26, 1985 [DE] Fed. Rep. of Germany ....... 3541718
May 7, 1986 [DE] Fed. Rep. of Germany ....... 3615447

[51] Int. Cl.⁴ .................. A01N 43/84; C07D 295/18
[52] U.S. Cl. ................................ 514/237.5; 514/212; 514/235.5; 540/524; 544/129; 544/130; 544/141; 544/158; 544/159; 544/163; 544/165; 544/167; 544/168; 544/169; 544/172; 544/174
[58] Field of Search .............. 544/158, 159, 163, 165, 544/167, 168, 169, 172, 174, 129, 130, 141; 514/237.5, 212, 235.5; 540/524

[56] References Cited

U.S. PATENT DOCUMENTS 4,337,252 6/1982 Astoin ................... 544/174

Primary Examiner—Robert W. Ramsuer
Attorney, Agent, or Firm—Sughrue, Mion, Zinn, Macpeak & Seas

[57] ABSTRACT

Compounds of the formula

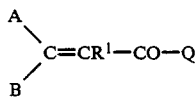

wherein
A is

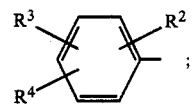

B is

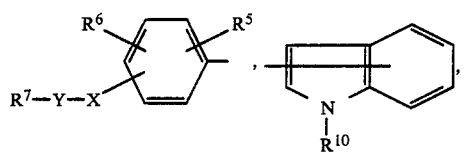

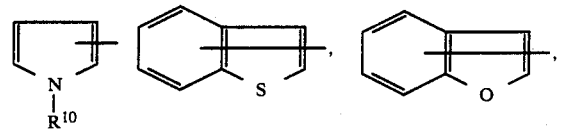

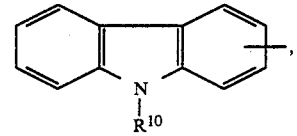

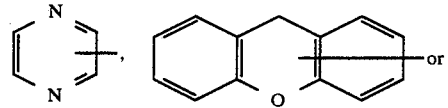

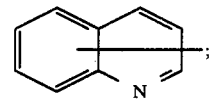

$R^1$ is hydrogen; halogen, cyano or optionally substituted $C_{1-4}$ alkyl; and
Q is $NR^8R^9$ or

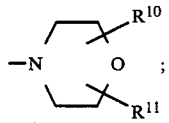

where $R^2$ to $R^{11}$ are substituents of various types. The compounds are useful as fungicides.

9 Claims, No Drawings

ACRYLIC ACID MORPHOLIDES, FUNGICIDAL COMPOSITIONS AND USE

This invention relates to novel acrylic acid amides, to methods of preparing these compounds, to microbicidal compositions containing them as active ingredients, and to a method of using them as microbicides, especially as fungicides.

More particularly, the present invention relates to a novel class of acrylic acid amides represented by the formula

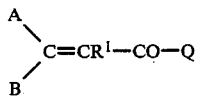  (I)

wherein
A is

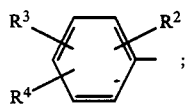;

B is

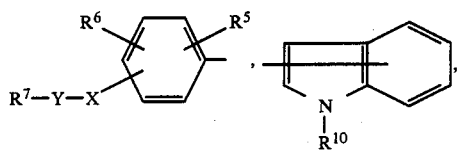,

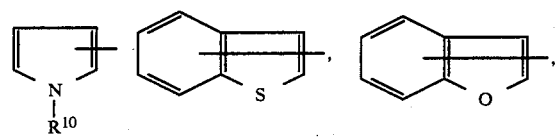,

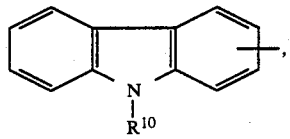,

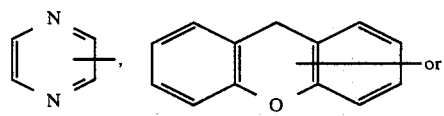

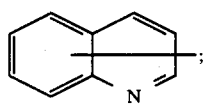;

$R^1$ is hydrogen, halogen, cyano or optionally substituted $C_{1-4}$ alkyl;
Q is $NR^8R^9$ or

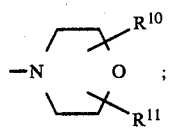;

$R^2$, $R^3$, $R^4$, $R^5$ and $R^6$, which may be identical to or different from each other, are each hydrogen, halogen, nitro, cyano, carboxyl, hydroxyl, $C_{1-4}$ alkoxycarbonyl, $CONR^{10}R^{11}$, $NR^{10}R^{11}$, $NR^{10}$-CO-$R^{11}$, or the following optionally substituted groups: $C_{1-6}$ alkyl, $C_{1-4}$ alkoxy, $C_{1-4}$ alkyl-$S(O)_p$ (where p=0, 1 or 2), $C_{3-7}$ cycloalkyl, phenyl, phenoxy or phenyl-$S(O)_p$ (where p=0, 1 or 2);

$R^8$ and $R^9$, which may be identical to or different from each other, are each hydrogen or the following optionally substituted groups: $C_{1-4}$ alkyl, $C_{3-7}$ cycloalkyl, phenyl, benzyl, $C_{3-7}$ alkenyl, $C_{3-7}$ alkynyl or alkoxyalkyl; $R^{10}$ and $R^{11}$, which may be identical to or different from each other, are each hydrogen, benzyl, phenyl or $C_{1-4}$ alkyl, or as substituents in hetaryl or hetaryloxy they may also be halogen, amino or mono- or di-lower alkylamino, or together they are —($CH_2$)$_4$— or —($CH_2$)$_5$;

X—Y is a single bond; —O—, —$S(O)_p$— (where p=0, 1 or 2), —$CONR^{10}CO$—, $NR^{10}$—$CONR^{10}$, —N=N—, —$CHR^{10}$—$S(O)_p$—, —$CHR^{10}O$—, (where p=0, 1 or 2), —$SO_2NR^{10}$—, —N=CH—, —$C_nH_{2n}$— (wherein n=1 to 10), —CH=CH—, —$NR^{10}CSNR^{11}$—, —$NR^{10}$—, —$R^{10}N$-$CHR^{11}$—, —$CHR^{10}NR^{11}$—, —O—$CHR^{10}$—, —$S(O)_p$—$CHR^{10}$—(where p=0, 1 or 2), —$NR^{10}SO_2$—, —$OSO_2$—, —$O_2SO$—, —$O_2S$—$NR^{10}$—, —C≡C—, —S—S—, —CHOH—, —CO—, —CH=NO, >C=$CH_2$, >C=CH—COOH, —NH—NH—, —N(O)=N—,

—CH———CH—,
\ /
O

—N=CH—, —$N(R^{10})$—N=CH—, —$N(R^{10})$—NH—CO—, —NH—CH=CH—, >CH—$C_6H_5$, —$COCH_2O$—, —CO—$CH_2S$—, —$OCH_2CO$—, —$SCH_2CO$—, —$CH_2CO$—, —CO—O, —O—CO—, —CO—S— or —S—CO—;

$R^7$ is hydrogen, $NR^{10}R^{11}$, $PO(OR^{10})(OR^{11})CH_2)_q$—CO—O—$R^{10}$ (where q=0, 1, 2, or 3), cyano, $CONR^{10}R^{11}$, $SO_2NR^{10}R^{11}$, tri-lower alkyl-silyl, hetaryl or hetaryloxy which is up to disubstituted by $R^{10}$ and $R^{11}$, [(1-formylamino-2,2,2-trichloro)ethyl]amino, 1-(3,4-dimethoxyphenyl)-3-(morpholin-4-yl)-prop-1-en-3-one, or the following optionally substituted groups: phenyl, alkyl of up to 12 carbon atoms optionally also interrupted by oxygen and/or sulfur atoms, cycloalkyl, optionally also interrupted by oxygen and/or sulfur atoms and/or nitrogen, penyl-substituted $C_{1-3}$ alkyl, $C_{2-6}$ alkenyl, $C_{2-6}$ alkynyl, $C_{5-8}$ cycloalkenyl or naphthyl, or when X - Y s a single bond, $R^7$ and $R^6$ may also together be a vicinal, optionally polysubstituted bridge of the formula —($CH_2$)$_n$-E— (wherein n=2 or 3), —(CH=CH)—D or

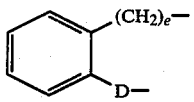

(where e=0 or 1), E is CH₂, O, S or NR¹⁰; and D is CH₂, O, S, NR¹⁰, —CH₂—CH—/₂ or —CH=CH—.

A preferred subgenus thereunder is constituted by those compounds of the formula I wherein A is

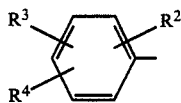

B is

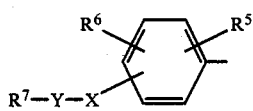

or optionally substituted p-biphenylyl;

R¹ is hydrogen; halogen, cyano or optionally substituted C₁₋₄ alkyl;

Q is

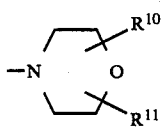

where R⁸ and R⁹, which may be identical to or different from each other, are each hydrogen or the optionally substituted groups: C₁₋₄ alkyl, C₃₋₇ cycloalkyl, phenyl, benzyl, C₃₋₄ alkenyl, propargyl or alkoxyalkyl, particularly C₁₋₄ alkyl; more particularly R⁸ is methyl and R⁹ is C₁₋₄ alkyl, especially methyl, ethyl or propyl; and R¹⁰ and R¹¹, which may be identical to or different from each other, are each hydrogen or C₁₋₄ alkyl, especially hydrogen, and R², R³, R⁴, R⁵ and R⁶, which may be identical to or different from each other, are each hydrogen, halogen, nitro, cyano, carboxyl, hydroxyl, C₁₋₄ alkoxycarbonyl, CONR¹⁰R¹¹, NR¹⁰R¹¹, NR¹⁰COR¹¹ or the optionally substituted groups: C₁₋₄ alkyl, C₁₋₄ alkoxy, C₁₋₄ alkyl-S(O)ₚ; (where p=0, 1 or 2); C₃₋₇ cycloalkyl, phenyl, phenoxy or phenyl(SO)p- (where p=0, 1 or 2).

The preferred combinations of definitions for X-Y and R⁷ are as follows:

(a) when X - Y is a single bond, R⁷ is optionally substituted C₄₋₁₂ alkyl, optionally substituted phenyl or C₃₋₇ cycloalkyl, optionally substituted naphthyl, hetaryl or hetaryloxy substituted up to twice by R¹⁰ and R¹¹, or PO(OR¹⁰)(OR¹¹);

(b) when X - Y is O or S(O)ₚ (where p=0, 1 or 2), R⁷ is hydrogen or substituted alkyl of up to 12 carbon atoms; optionally substituted phenyl, C₃₋₇ cycloalkyl, naphthyl, PO(OR¹⁰)(OR¹¹), COOR¹⁰ (wherein R¹⁰ ≠ H), optionally substituted pyridyl or tri-lower alkylsilyl;

(c) when X - Y is NR¹⁰CO, R⁷ is optionally substituted phenyl, benzyl, naphthyl or cycloalkyl; hetaryl or hetaryloxy which is substituted up to twice by R¹⁰ and R¹¹, or NR¹⁰R¹¹;

(d) when X - Y is NR¹⁰CSNR¹¹ or NR¹⁰CONR¹¹, R⁷ is hydrogen, optionally substituted alkyl, phenyl, benzyl, naphthyl or C₃₋₇ cycloalkyl; or NR¹⁰R¹¹;

(e) when X - Y is N=N, R⁷ is optionally substituted phenyl or naphthyl;

(f) when X - Y is CHR¹⁰—NR¹¹; —CHR¹⁰—O— or —CHR¹⁰S—, R⁷ is hydrogen, optionally substituted C₁₋₁₂ alkyl, phenyl, benzyl, C₃₋₇ cycloalkyl or naphthyl; PO(OR¹⁰)(OR¹¹) or COOR¹⁰ (where R¹⁰≠H);

(g) when X - Y is SO₂NR¹⁰, R⁷ is hydrogen; ; or optionally substituted C₁₋₁₂ alkyl, phenyl, benzyl, naphthyl or C₃₋₇ cycloalkyl;

(h) when X - Y is N=CH, R⁷ is optionally substituted phenyl, benzyl or naphthyl;

(i) when X - Y is (CH₂)n (where n=1, 2, 3 or 4); R⁷ is cyano; COOR¹⁰; PO(OR¹⁰)(OR¹¹); NR¹⁰R¹¹); optionally substituted phenyl, C₃₋₇ cycloalkyl or naphthyl; or hetaryl substituted up to twice by R¹⁰ and R¹¹;

(j) when X - Y is CH=CH, R⁷ is optionally substituted C₁₋₁₂ alkyl, phenyl, benzyl or naphthyl;

(k) when X - Y is NR¹⁰, R⁷ is PO(OR¹⁰)(OR¹¹); COOR¹¹ (where R¹¹≠H); or optionally substituted phenyl, benzyl, naphthyl or C₃₋₇ cycloalkyl;

(l) when X - Y is R¹⁰NCHR¹¹; O-CHR¹⁰ or S(O)ₚCHR¹⁰ (where p=0, 1 or 2), R⁷ is substituted C₁₋₄ alkyl; PO(OR¹⁰)(OR¹¹) tri-lower alkylsilyl; optionally substituted C₅₋₁₂ alkyl, phenyl, benzyl, C₃₋₇ cycloalkyl, naphthyl, or hetaryl substituted up to twice by R¹⁰ and R¹¹, or (CH₂)qCOOR¹⁰ (where q=0, 1, 2 or 3);

(m) when X - Y is NR¹⁰SO₂ or O-SO₂, R⁷ is optionally substituted C₁₋₁₂ alkyl, phenyl, benzyl, naphthyl or C₃₋₇ cycloalkyl; NR¹⁰R¹¹; hetaryl substituted up to twice by R¹⁰ and R¹¹, or (CH₂)q—COOR¹⁰ (where q=0, 1, 2 or 3);

(n) when X - Y is O-CO or S-CO, R⁷ is hydrogen; NR¹⁰R¹¹; optionally substituted alkyl of up to 12 carbon atoms, phenyl, benzyl, cycloalkyl or naphthyl;

(o) when X - Y is CO-O, CO-S, or CONR¹⁰, R⁷ is substituted C₁₋₄ alkyl; or optionally substituted C₅₋₁₂ alkyl, phenyl, benzyl, cycloalkyl or naphthyl.

In the definitions given above, the radicals and groups in each case may be identical to or different from each other, that is, if one of the substituents mentioned above occurs several times in a particular molecular, the definition each time may be freely selected with the scope of the definitions.

Of the substituents in A (R², R³ and R⁴) and of the substituents in B (R⁵ and R⁶), as a rule only one represents carboxyl, C₁₋₄ alkoxycarbonyl, CONR¹⁰R¹¹, NR¹⁰R¹¹, NR¹⁰—COR¹¹, C₃₋₇ cycloalkyl, phenyl, phenoxy or phenyl-S(O)ₚ.

The term "alkyl" as used herein means straight-chained or branched C₁₋₁₂ alkyl radicals, while the term "lower alkyl" refers to the C₁₋₄ alkyl radicals and includes methyl, ethyl, n-propyl, isopropyl, n-butyl, sec.-butyl, tert-butyl, isobutyl and the isomeric pentyl, hexyl, heptyl, octyl, nonyl, decyl, undecyl and dodecyl radicals. The above definition also applies if the alkyl radical is substituted and/or is part of an alkoxyalkyl, alkoxycarbonyl, carbamoyl, alkoxy, alkylthio, alkylsulfinyl, alkylsulfonyl, monoalkylamino, aralkyl, alkylthiomethyl or dialkylamino group or the alkyl radical is bonded as a substituent to an aromatic, heterocyclic or carbocyclic system.

The term "substituted alkyl" means alkyl radicals which are mono- or polysubstituted by hydroxyl, alkoxy, mercapto, halogen, alkylthio, nitro, cyano or amino, mono- or di-lower akkylamino. Halogen, hydroxyl, alkoxy and cyano are preferred; particular mention should be made of trifluoromethyl trichloromethyl and —CCl=CHCl.

Halogens are fluorine, chlorine, bromine and iodine, preferably fluorine, chlorine and bromine.

"$C_{3-7}$ cycloalkyl" means cyclopropyl, cyclobutyl, cyclopentyl, cyclohexyl or cycloheptyl. Cyclopropyl, cyclopentyl or cyclohexyl are preferred.

The cycloalkyl groups are preferably unsubstituted or substituted up to three times by alkyl, halogen (preferably fluorine or chlorine)), hydroxyl, oxo or amino. Cycloalkyl groups interrupted by oxygen atoms include, for example:

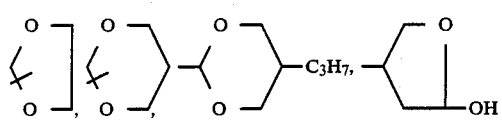

Substituted phenyl or substituted naphthyl are preferably systems substituted up to three times by halogen, $C_{1-4}$ alkyl, alkylthio, alkoxy, nitro, cyano, amino, monoalkylamino, dialkylamino, haloalkyl, haloalkylthio, haloalkoxy, carboxy or alkoxycarbonyl.

The term "hetaryl" means, in particular, N-heterocyclic groups which are bonded to the connecting member X - Y via a cyclic nitrogen atom or via a carbon atom. Hetaryl includes not only aromatic but also wholly or partially hydrogenated groups and also condensed systems which contain benzene rings, such as pyrazolyl, pyrazinyl, imidazolyl, 1,2,4-triazolyl, morpholinyl, piperidinyl, pyrrolyl, pyrrolidinyl, 2,5-dioxopyrrolidinyl, 1,3-isoindoldionyl and pyridinyl radicals, and radicals derived from indole, benzofuran, quinoline or benzothiophene.

Further hetaryl groups are exemplified by the following:

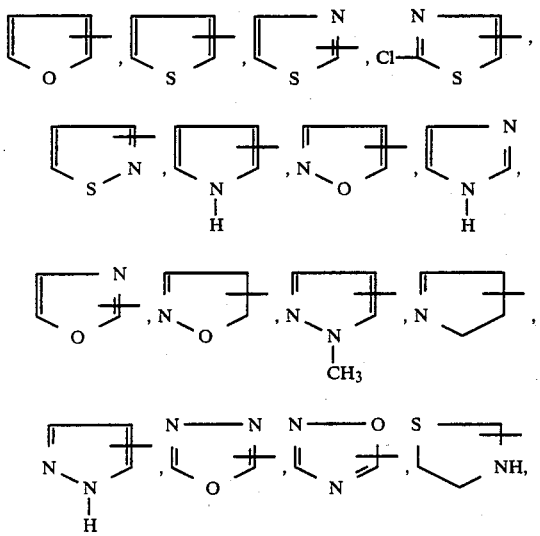

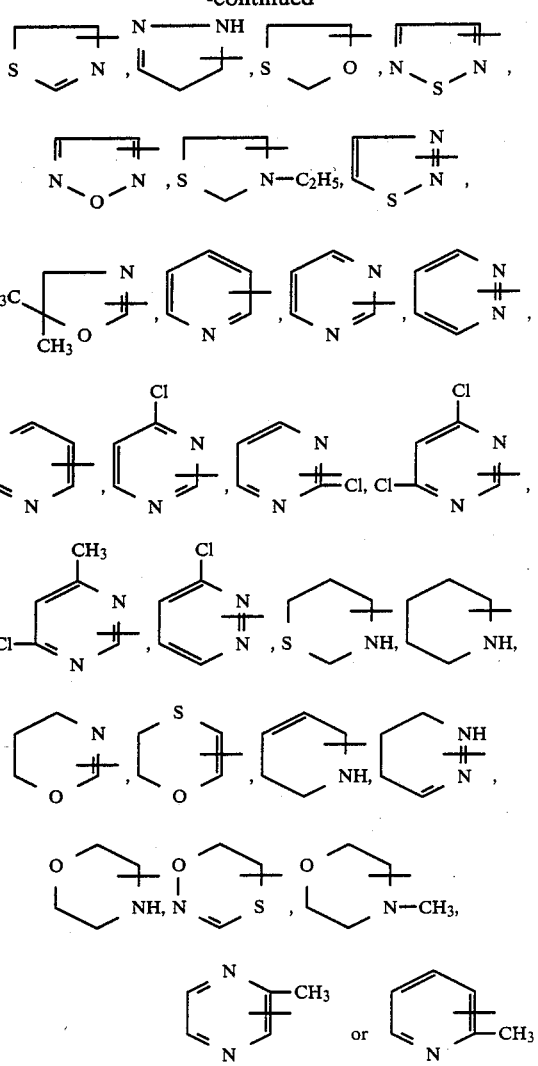

The substituents attached to the phenyl radicals A and B are preferably (with the exception of the substituents attached to the bridge X - Y) halogen, nitro, amino, methylthiomethyl, methoxymethl, methylthio, methoxy, cyanomethyl, ethoxy, ethylthio, $C_{1-4}$ alkyl, acetamido, methylamino or dimethylamino.

The substituents are preferably attached to the two phenyl rings A and B in the meta or para position. Preferred substitution patterns for the ring A include, in addition to the unsubstituted system: 3,4-dimethoxy, 3-ethoxy-4-methoxy, 3-chloro-4-methoxy, 3,5-dichloro-4-amino, 3-bromo-4-methoxy, 3-methyl-4-methoxy, 3-ethyl-4-methoxy, 3-propyl-4-methoxy, 3-bromo-4-dimethylamino, 3,4-dimethyl, 3-amino-4-methoxy, 3-acetamido, 3-acetamido-4-methoxy, 3-acetamido-4-chloro, 3,5-dimethyl-4-methoxy, 4-methoxy 4-ethoxy, 3-methoxy-4methyl and 3-bromo-4-amino.

The group Q is preferably derived from the following amines: dimethylamine, diethylamine, methylethylamine, methylpropylamine, methylbutylmmine, morpholine, 2-methylmorpholine, 2,6-di-methylmorpholine, N-(2-hydroxyethyl)-N-methylamine, N-(2-hydroxyethyl)-N-ethylamine.

When A and B in formula I are different, the compounds of the formula I may occur as cis/trans isomers.

Formula I in this case will include both the individual isomers and also mixtures of the cis and trans compounds.

Moreover, the groups A and B may be affected in their free rotation about the axis of the single bond by steric or other secondary reciprocal effects; their effects may cause atropisomerism. Thus, the invention also includes the atropisomeric structures of (I).

Some typical compounds of the present invention are shown in the following Tables.

TABLE A

Compounds of formula

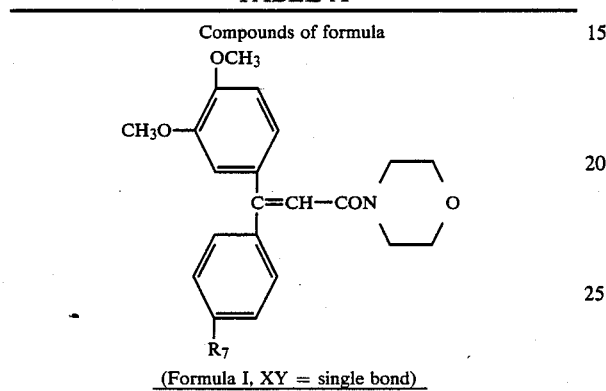

(Formula I, XY = single bond)

| No. | R₇ |
|---|---|
| 1 | -n-C₃H₇ |
| 2 | -n-C₄H₉ |
| 3 | —CH(CH₃)C₂H₅ |
| 4 | —CH₂CH(CH₃)₂ |
| 5 | -n-C₅H₁₁ |
| 6 | -n-C₆H₁₃ |
| 7 | cyclohexyl |
| 8 | -C₆H₄-C₂H₅ |
| 9 | -C₆H₄-Cl |
| 10 | -C₆H₅ |
| 11 | cyclohexenyl |
| 12 | morpholinyl (N,O) |

TABLE A-continued

Compounds of formula

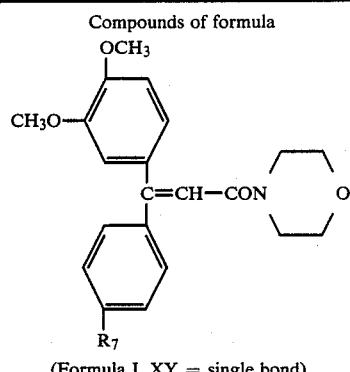

(Formula I, XY = single bond)

| No. | R₇ |
|---|---|
| 13 | benzimidazolyl (NH) |

TABLE B

Compounds of formula

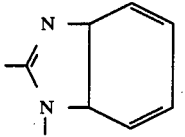

(Formula I, XY = —O—)

| No. | R₇ | Position of OR⁷ |
|---|---|---|
| 1 | -n-C₄H₉ | 4 |
| 2 | -n-C₅H₁₁ | 4 |
| 3 | —CCl=CHCl | 4 |
| 4 | -C₆H₄-Cl | 4 |
| 5 | -C₆H₄-CO₂CH₃ | 4 |
| 6 | -C₆H₄-CN | 4 |
| 7 | -C₆H₄-Cl (3-position) | 4 |

TABLE B-continued

Compounds of formula

[Structure: 3,4-dimethoxyphenyl-C(=CH-CON-morpholine)-phenyl-OR⁷]

(Formula I, XY = —O—)

| No. | R₇ | Position of OR⁷ |
|---|---|---|
| 8 | 4-chloro-3-methylphenyl | 4 |
| 9 | 4-fluorophenyl | 4 |
| 10 | —C₆H₅ | 3 |
| 11 | 6-chloropyridazin-3-yl (N=N) | 4 |
| 12 | 4-fluorophenyl | 3 |

TABLE C

Compounds of formula

[Structure: 3,4-dimethoxyphenyl-C(=CH-COQ)-phenyl-S(O)ₚ-phenyl-R]

| No. | R | P | Q |
|---|---|---|---|
| 1 | Cl | 0 | —N(morpholine)O |
| 2 | Br | 0 | —N(morpholine)O |
| 3 | Cl | 0 | —N(CH₃)(C₂H₅) |
| 4 | Cl | 1 | " |
| 5 | Cl | 2 | " |
| 6 | Cl | 1 | —N(morpholine)O |
| 7 | Cl | 2 | —N(morpholine)O |

TABLE D

Compounds of formula

[Structure: 3,4-dimethoxyphenyl-C(=CHCOQ)-phenyl-XYR⁷]

| No. | R⁷—YX— | Q |
|---|---|---|
| 1 | C₆H₅— | —N(CH₃)(C₂H₅) |
| 2 | C₆H₅—N=N— | —N(morpholine)O |
| 3 | C₆H₅—CH₂O— | " |
| 4 | C₆H₅—OCH₂— | " |
| 5 | C₆H₅—N=N— | —N(C₂H₅)(C₂H₅) |

TABLE D-continued

Compounds of formula

| No. | R⁷—YX— | Q |
|---|---|---|
| 6 | C₆H₅—CH₂O— | —N(CH₃)(C₂H₅) |
| 7 | (furyl)—CO—O— | morpholino |
| 8 | (thienyl)—CO—O— | " |
| 9 | (benzothiazolyl)—SCH₂— | " |
| 10 | (benzothiazolyl)—S— | morpholino |

In general, we have found that the compounds of the formula

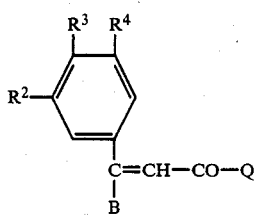

particularly those where Q is morpholino or methylethylamino and $R^2$ and $R^3$ are methoxy, and $R^4$ is hydrogen may vary considerably with regard to the group B without impairing the fungicidal activity. The same is true of the combinations of substituents $R^2/R^3/R^4 = C_2H_5O/CH_3O/H$;  Cl/CH₃O/H; Br/CH₃O/H;  CH₃/CH₃O/H ; Cl/NH₂/Cl; CH₃O/Cl/H.

The compounds embraced by formula I may be prepared by the following methods which involve well known chemical synthesis principles:

Method A

By reacting an acrylic acid o the formula

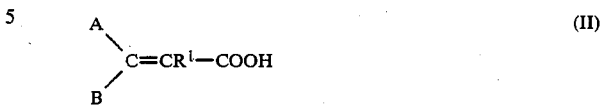

wherein A, B and $R^1$ have the meaning previously defined, or a reactive derivative of (II) optionally prepared in situ, with a compound of the formula $$HQ \qquad (III)$$

wherein Q has the meanings previously defined.

This method, which thus involves acylation of a compound of the formula III with a carboxylic acid of the formula II, is advantageously carried out in the presence of an agent which activates the acid II or of a dehydrating agent, or with a reactive derivative of the carboxylic acid II or of the compound III.

Examples of reactive derivatives of a carboxylic acid of the formula II, optionally prepared n the reaction mixture, include the alkyl, aryl, aralkyl or thioesters thereof, such as the methyl, ethyl, phenyl or benzyl esters, the imidazolides; the acid halides such as the acid chloride or bromide, the anhydrides, the mixed anhydrides with aliphatic or aromatic carboxylic, sulfenic, sulfinic and sulfonic acids or with carbonic acid esters, for instance with acetic acid, propinoic acid, p-toluenesulfonic acid or O-ethylcarbonic acid, or the N-hydroxyimide esters thereof. Examples of suitable reactive derivatives of an amine of the formula III, optionally prepared in the reaction mixture, include the "phosphorazo derivatives."

Examples of acid-activating or dehydrating agents include chloroformates such as ethyl chloroformate, phosphorus pentoxide, N,N-dicyclohexylcarbodiimide, N,N′-carbonyldiimidazole or N,N′-thionyldiimidazole.

The reaction is advantageously carried out in a solvent or mixture of solvents such as methylene chloride, chloroform, carbon tetrachloride, ether, tetrahydrofuran, dioxane, benzene, toluene, acetonitrile or dimethylformamide, optionally in the presence of an inorganic base such as sodium carbonate or a tertiary organic base such as triethylamine or pyridine, which may simultaneously serve as solvent, and optionally in the presence of an acid-activating agent, at temperatures between −25° C. and 150° C., but preferably at temperatures between −10° C. and the boiling point of the reaction mixture. A reactive derivative of compound of the formula II or III, optionally formed in the reaction mixture, need not be isolated; moreover, the reaction may also be carried out in an excess of the compound of the formula III which functions as the solvent medium.

Cis/trans isomer mixtures obtained according to the invention may, if desired, subsequently be separated by conventional methods into he corresponding cis and trans isomers. The same applies to any atropisomers obtained.

Method B

By reacting a ketone of the formula (IV) with a phosphono acetic acid derivative of the formula (V) wherein R′ is preferably lower alkyl, using the method of Wittig and Horner

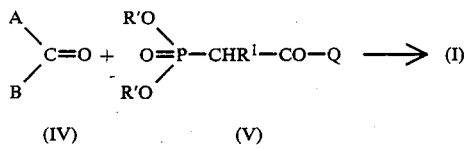

(IV)      (V)

The separation of isomers is carried out preferably by fractional crystallization, for example from methanol, ethanol, isopropanol, methanol/water or ethanol/petroleum ether.

Compounds of the formula I comprising basic groups may, if desired, be converted into acid addition salts, preferably with inorganic acids such as hydrochloric, hydrobromic, sulfuric or phosphoric acid.

The acrylic acid derivatives of the formula II are also new. They may be prepared by known methods. Starting compounds of the formula II in which A and B have the meanings previously defined may be prepared, starting from a ketone of formula IV, by methods described in the literature.

Preparation of compounds of the formula II:

(a) By reacting IV with an α-halocarbonate VI, followed by hydrolysis:

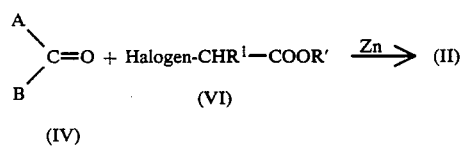

(IV)

(b) By reacting IV with a CH-acidic component according to Knoevenagel, illustrated here with reference to the reaction of IV with a nitrile VII and subsequent hydrolysis of the acrylonitrile VIII to yield the carboxylic acid II:

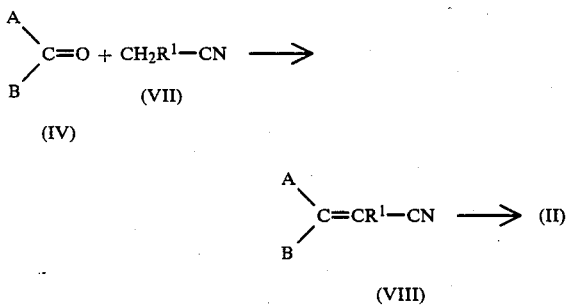

(c) Acrylic acids of the formula II may also be prepared according to Wittig-Horner, starting from a ketone IV by reacting it with a phosphonoacetic acid of the formula IX and subsequent hydrolysis of the ester X:

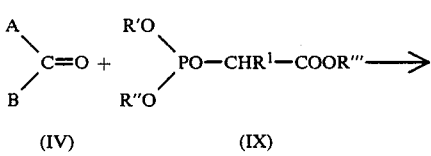

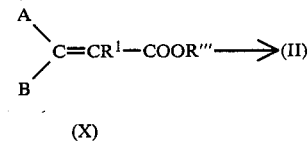

(X)

where R', R" and R''' are identical or different lower alkyl groups.

Method C

By synthesizing or introducing the group —XY-$R^7$ in a compound of the formula

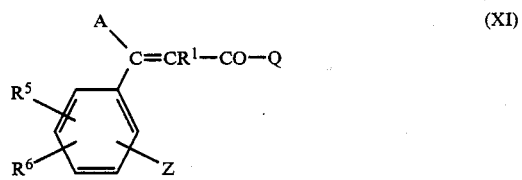

wherein A, Q, $R^1$, $R^5$ and $R^6$ have the meanings previously defined and Z is hydrogen or a substituent which can be exchanged for -XY-$R^7$ (where X, Y and $R^7$ have the meanings previously defined) or which can be converted into -XY-$R^7$.

The reactions to synthesize or introduce -XY-$R^7$ may be of different types. Examples of such reactions include, in particular, reactions of substitution, addition, esterification and amidation, oxidation and reduction.

(a) Substituents of the formula X-Y-$R^7$ which are attached to the phenyl group B via a nitrogen atom, such s —$NR^{10}$—CO or the like, may be prepared stating from amino compounds using methods which are generally known. The amino compounds may in turn easily be obtained, for example, by reducing the corresponding aromatic nitro compounds.

(b) Phenolic OH groups in part B of the molecule may be converted by usual methods to prepare compounds wherein XY is —O— or compounds wherein the group —XY—$R^7$ is attached to the benzene ring via an oxygen atom.

(c) Substituents of the formula -X-Y-$R^7$ wherein -XY- is $S(O)_p$ may, for example, be obtained from the corresponding mercapto compounds (XI, Z=SH) by substitution, using conventional methods (p=0) and optional oxidation to obtain the sulfoxides (p=1) or sulfones (p =2).

(d) If the bridge member —XY— has a $CH_2$ group attached to the benzene ring, a corresponding compound XI wherein Z is —$CH_2$Hal (Hal=Cl, Br, I) may be substituted by nucleophilic substitution reactions, e.g. with phenoxide or thiophenoxide, or with other reactants which may be linked to the $CH_2$ group while hydrogen halide is split off.

(e) If -XY-$R^7$ represents a group attached to the benzene ring via —CO—, corresponding compounds XI wherein Z=COOH may be functionalized.

(f) In compounds XI wherein Z represents a leaving group, such as a reactive halogen, the halogen atom may be functionalized, while hydrogen halide is split off, by reaction with corresponding nucleophilic compounds H-XY-$R^7$.

(g) An important method of functionalizing compounds of the formula XI wherein Z is iodine or bromine, $R^1$ is hydrogen and the compound XI does not contain any other bromine or iodine atoms, consists in reacting the corresponding compounds XI with a corresponding alkene, using the method of Heck (the details are described under method D). A bond is established between the benzene ring and the alkene while hydrogen halide is split off, and optionally the double bond is shifted, for example when the reaction is carried out with cyclohexene. By using carboxy- or alkoxycarbonyl-substituted alkenes such as acrylic acid or cinnamic acid or the lower alkylesters thereof, optionally with hydrolysis and decarboxylation, the position of the bond may be controlled. The reaction sequence is as follows:

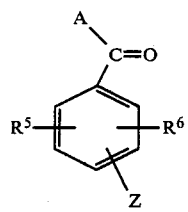

(XII)

wherein A, $R^5$, $R^6$ and Z have the meanings previously defined, or for acrylic acids or acrylic acid esters of the formula

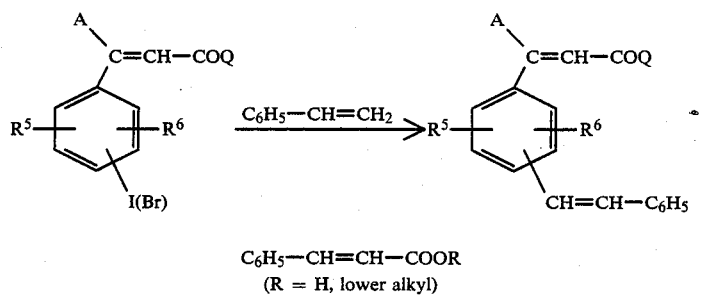

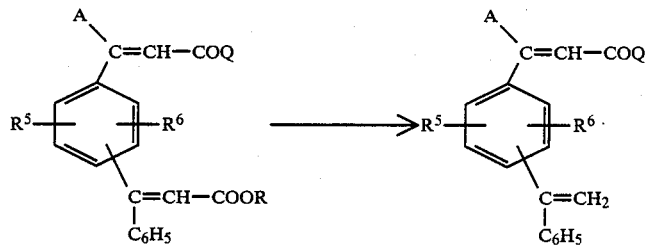

The above reaction methods for preparing acrylic acid amides of the formula I are summarized in the synthesis scheme shown below.

Many of the starting compounds for the end products of the present invention are known. Those which are not known may be obtained by known methods, including some of the methods described above.

Thus, the reactions given for compounds XI in Method C may also be used for the precursors, for instance for benzophenones of the formula

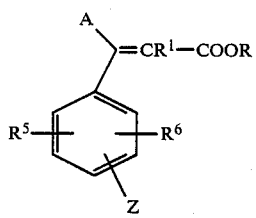

(XIII)

wherein A, $R^1$, $R^5$, $R^6$ and Z have the meanings previously defined and R is H or lower alkyl. Compounds XII and XIII wherein Z is OH may be obtained, inter alia by conventional ether cleavage from corresponding compounds wherein Z is alkoxy, such as $CH_3O$.

Summarized representation of methods A, B and C for the synthesis of compounds of the formula I:

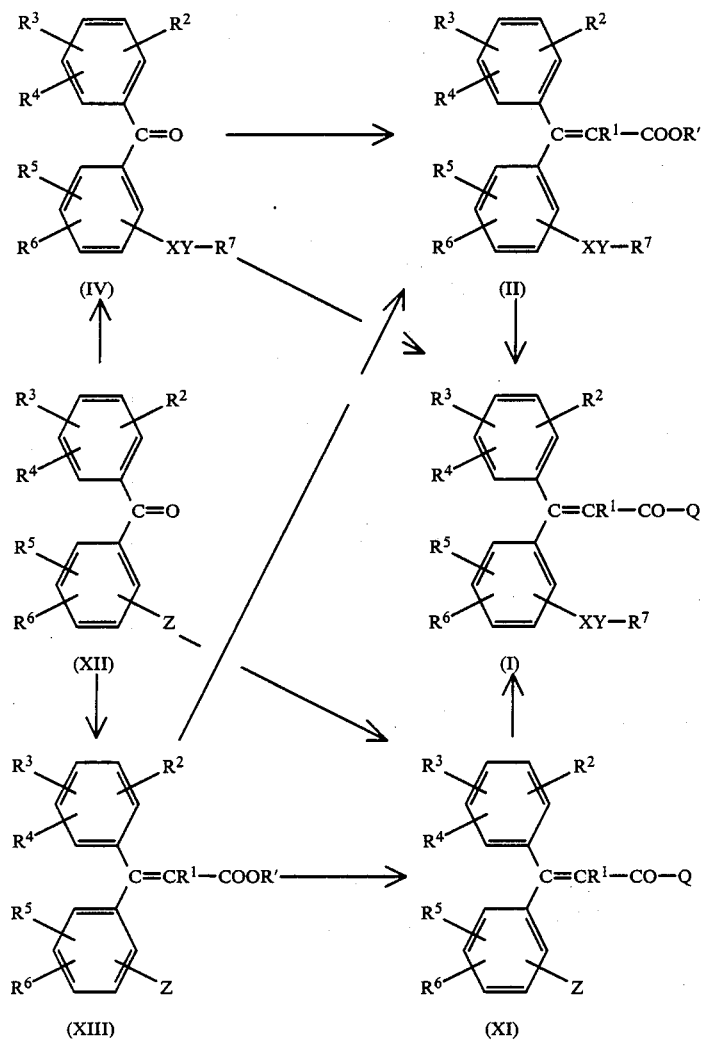

Method D

For the preparation of a compound of the formula

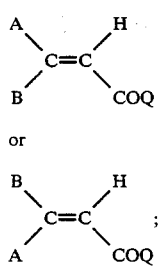  (Ia)

or

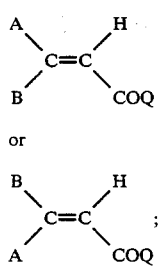  (Ib)

by reacting a compound of the formula

B—CH=CH—COQ  (XIVa)

or

A—CH=CH—COQ  (XIVb)

in the presence of a palladium catalyst with a corresponding compound of the formula A—Hal  or  B—Hal (XVa)       (XVb)

wherein Hal represents chlorine, bromine or iodine and A and B have the meanings previously defined.

The reaction, a palladium (O) - catalyzed vinylilation of halobenzenes, has become known as a Heck reaction (R. F. Heck, Organic Reactions, Vol. 27, 345 H). Particularly suitable halobenzenes are correspondingly substituted iodo-benzenes and bromo-benzenes of the formula XVa/XVb.

The reaction may be performed either with or without a solvent. Both polar and non-polar solvents are suitable, for instance nitriles such as acetonitrile or propionitrile; alcohols such as methanol, ethanol, propanol or isopropanol; ketones such as acetone or methyl ethyl ketone; ethers such as diethyl ether, tetrahydrofuran, diisopropyl ether, glymes, diglymes or the like; amides such a dimethylformamide, N- methyl-pyrrolidone or hexamethylphosphoric acid triamide; aromatic compounds such as benzene, toluene, xylene or chlorobenzene.

The presence of small quantities of water is generally not a problem.

The reaction may be performed at temperatures between room temperature and the boiling point of the solvent. It may also be carried out under pressure at even higher temperatures if a sealed apparatus is used. A temperature range from 30 to 160° C. is preferred.

At a reaction temperature of about 100° C., a quantity of 1 mol-% of the palladium catalyst (based on the quantity of halobenzene XV) is sufficient. Larger quantities of catalyst may improve the speed of the reaction or enable the reaction temperature to be reduced.

In the course of the reaction, a hydrohalic acid is released, which is neutralized with bases. If carboxylic acids are used as educts, it is advantageous to add a quantity of base equivalent to the carboxy function. Examples of suitable bases include inorganic bases such as soda, sodium acetate, sodium bicarbonate or the like, amines such as triethylamine or triethylene=diamine or the like, as well as heterocyclic amines such as pyridine, quinoline or the like.

The palladium catalyst used may be either one of the standard laboratory Pd-C catalysts or a palladium (II) salt, such as palladium acetate or a palladium halide. The salts are reduced under the reaction conditions to yield palladium-(O). It is often advantageous, particularly when using palladium (II) salts, to add a complexing agent such as a triarylphosphine.

The newly introduced group A or B enters predominantly in the transposition relative to the group COQ. Therefore, the desired isomer may be produced by suitably selecting the starting products.

The isomers are named according to the E/Z nomenclature system, the four substituents being arranged in the order of declining priority in accordance with the Cahn-Ingold-Prelog-System [Angewante Chemie 78 (1966) 413; J. Chem. Soc. 1951, 612; Experimenta 12 (1956), 81; Bayer/Walter, Lehrbuch der organischen Chemie, 19. Aufl. S. Hirzel Verlag Stuttgart, p. 69; Pure-Appl. Chem. 45, 11–30 (1976); J. Org. Chem. 1970, 2849].

The E/Z isomers are in equilibrium as a result of the effects of light by Lewis acid catalysis, thermally or by base catalysis at elevated temperature.

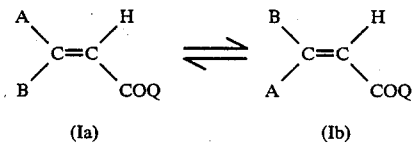

(Ia)         (Ib)

The compounds of the formula Ia can therefore be regarded as useful precursors for the fungicidally active form Ib. In open air conditions in particular, the inactive isomers Ia are able to make the active form Ib available via the equilibrium Ia/Ib.

The compounds XIV needed as starting materials may be obtained by reacting an aldehyde of the formula

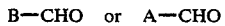

with a suitable phosphonoacetic acid derivative according to Wittig-Horner.

Moreover, the compounds XIV may be obtained by the Heck reaction with Pd(0) catalysis from corresponding acrylic acid derivatives of the formula

 (XVI)

and a compound XVb or XVa.

The reaction according to method D above may also be combined with the preparation of the starting substance, that is, it may be carried out as a "one-pot reaction". First, a halobenzene of the formula XVa of XVb is reacted with an acrylic acid of the formula XVI under the conditions of the Heck reaction to yield a cinnamic acid derivative of the formula XIVa or XIVb, the halobenzene being used up completely. Then, more halobenzene XVb or XVa is added, which reacts in the second stage with XIVa or XIVb to yield the product Ib or Ia. The equivalents of base used in the "one-pot process" are calculated so that they are able to bind all the hydrohalic acid released in the reaction.

The following examples illustrate the present invention and will enable others skilled in the art to understand it more completely. It should be understood, however, that the invention is not limited solely to the particular examples given below.

Many acrylic acid amides of the formula I may only be isolated in the form of an oil, a resin or a solidifying resin. Such compounds are therefore characterized by their Rf-value which is determined by thin-layer chromatography with TLC-plates of the polygram SIL G/UV 254 type made by Macherey-Nagel.

EXAMPLE 1:

1,4-Bis-[1-(3,4-dimethoxyphenyl)-2-(morpholinocarbonyl)-1-vinyl ]-benzene (a) 1,4-Bis-(3,4-dimethoxybenzoyl)-benzene Under exclusion of moisture and while cooling with ice, first terephthalic acid dichloride (10.15 g; 0.05 mol) and then veratrole (13.8 g; 0.1 mol) were added dropwise to aluminum chloride (16 g; 0.12 mol) in dichloroethane (50 ml) accompanied by stirring. Then, the mixture was stirred for 1 day at room temperature.

Water/HCl was then added to the reaction mixture, and it was extracted with chloroform (100 ml). After the organic extract had been dried it was concentrated by evaporation, leaving a slowly crystallizing oil which was triturated with a little toluene/methanol.

After it had been allowed to stand for 1 hour, the product was suction-filtered off. Yield: 9.0 g of the title compound; m.p. 173°–188° C. (the substance began to sinter above 140°).

(b) 1,4-Bis-[1-(3,4-dimethoxyphenyl)-2-carboxy-1-vinyl ]-benzene

Triethylphosphonoacetate (11.2 g; 0.05 mol) was added dropwise to a suspension of sodium hydride (80%; 1.5 g; 0.05 mol) in dimethoxyethane (50 ml) while stirring and cooling with ice. The,, 1,4-bis(3,4-dimethoxybenzoyl)-benzene was added (8.9 g; 0.022 mo), and the mixture was heated at 100° C. for 5 hours. After evaporation, the residue was shaken with toluene/water, and the organic phase was dried and evaporated.

11.0 g of a residue was obtained, which was mixed with a mixture of KOH, methanol and water (8.4 g KOH, 100 ml methanol, 5 ml water) and then heated at the boiling point for 2 hours.

The residue obtained after evaporation was taken up in water, extracted with toluene and then precipitated with hydrochloric acid as a resin which was recrystallized from toluene.

Yield: 8.0 g of the title compound as a slowly crystallizing resin which was used in the next reaction without any further purification.

(c) 1,4-Bis-[1-(3,4-dimethoxyphenyl)-2-(morpholino-carbonyl)-1-vinyl]benzene

Carbonyl diimidazole (5.8 g; 0.036 mol) was quickly added, while stirring, to a suspension of 1,4-bis-[1-(3,4-dimethoxyphenyl)-2-carboxyl-1-vinyl]-benzene (8.1 g; 0.0165 mol) in tetrahydrofuran (50 ml) at room temperature. The suspended matter dissolved, accompanied by considerable evolution of $CO_2$ Morpholine was added (3.1 g; 0.036 mol), and the mixture was boiled for 1 hour. After the solvent had been distilled off, the residue was taken up in toluene/ethyl acetate (1:1), washed with water and purified on silica gel with toluene/acetone (9:1).

Yield: 2 g of the purified title compound with an Rf-value of 0.783 (in toluene/acetone =3:7).

EXAMPLE 2

1,3-Bis-[1-(3,4-dimethoxyphenyl)-2-(morpholinocarbonyl)-1-vinyl]-benzene

Analogous to Example 1, the title compound was obtained as a resin with Rf=0.27 (silica gel, toluene/acetone 7:3), starting from isophthalic acid dichloride and veratrole.

EXAMPLE 3

3-[2-(4-Chlorophenoxymethyl)-4-methoxyphenyl]-3-phenylacrylic acid morpholide (a) 3-Bromomethyl-4-methoxybenzophenone A solution of 3-Methyl-4-methoxy-benzophenone (34 g) in a mixture of carbon tetrachloride (100 ml) and carbon disulfide (5 ml) was boiled while stirring and irradiating with a UV-lamp.

Over a period of 3 hours, bromine (24.0 g) in carbon tetrachloride (10 ml) was added dropwise to this solution which was then irradiated and boiled for another hour.

The mixture was then extracted with water, dried and evaporated, and the residue was recrystallized from methanol. Yield: 32.4 g of the title compound in the form of crystals, m.p. 98°–100° C.

(b) 3-(4-Chlorophenoxymethyl)-4-methoxybenzophenone

3-Bromomethyl-4-methoxybenzophenone (15.25 g) and sodium 4-chlorophenoxide (7.6 g) in acetonitrile (70 ml) were boiled for 33 hours, while stirring.

After the solvent was evaporated, the residue was taken up in toluene, the solution was washed with water and then evaporated again, and the residue was recrystallized from methanol.

Yield: 15 g of the title compound in the form of crystals, m.p. 103° C.

(c) 3-[3-(4-Chlorophenoxymethy)-4-methoxyphenyl]-3-phenylacrylic acid morpholide Diethylphosphonoacetic acid morpholide (8.8 g) was added dropwise to a solution of sodium hydride (80%, 1.2 g) in tetrahydrofuran (50ml) while stirring, and the mixture was stirred for 30 minutes at room temperature, after which 3-(4-chlorophenoxymethyl)-4-methoxybenzophenone (10 g) was added. The resulting mixture was boiled for 2 hours.

After the reaction mixture had been evaporated, the residue was shaken with water/methylene chloride, and the organic phase was separated, dried and evaporated. The title compound was obtained in the form of a resin.

Yield: 8.8 g, Rf-value 0.79 (silica gel, toluene/acetone 3:7).

EXAMPLE 4

3-[4-(4-Chlorophenylmercapto)-phenyl]-3-(3,4-dimethoxyphenyl)-acrylic acid morpholide (a) 3,4-Dimethoxy-4'-fluoro-benzophenone Veratrole (29.3 g) was added, while stirring, to a mixture of aluminum chloride (34 g) and 4-fluorobenzoyl chloride (35 g) which had been cooled to 0° C., and the resulting mixture allowed to stand for 12 hours at room temperature. It was then boiled for 1 hour. The reaction mixture was then decomposed with water/HCl and extracted with chloroform.

The organic phase was dried and evaporated. The residue was triturated into crystalline form with methanol. Yield: 46 g of the title compound in the form of crystals, m.p. 112°–115° C.

(b) 3,4-Dimethoxy-4'-(4-chlorophenylthio)-benzophenone

Sodium p-chlorothiophenoxide was prepared from p-chlorothiophenol (4.3 g) in methanol (10 ml) and sodium methoxide (5.4 g of a 30% sodium methoxide solution) by evaporation in a rotary evaporator. The resulting salt was dissolved, together with 3,4-dimethoxy-4'-fluorobenzophenone (7.8 g) in dimethylformamide (30 ml), and the solution was heated at 100° C. for 3 hours. Then, the reaction mixture was poured into water, and the crystals which precipitated were recrystallized from ethanol.

Yield: 7.4 g of the title compound in the form of shiny crystals, m.p. 118°–120° C.

(c) 3-[4-(4-Chlorophenylmercapto)-phenyl]-3-(3,4-dimethoxyphenyl)-acrylic acid morpholide Diethylphosphonoacetic acid morpholid (6.6 g) was added to a suspension of sodium hydride (80%, 0.75 g) in tetrahyrrofuran (40 ml) while stirring, and stirring was continued for 1 hour.

Then, 3,4-dimethoxy-4'-(4-chlorophenylthio)-benzophenone (7.3 g) was added, and the mixture was boiled for 2 hours. The solvent was distilled off, and the residue was extracted with water/ethyl acetate.

The resin isolated from the organic phase was purified on silica gel with toluene/acetone (9:1).

Yield: 5 g of the title compound in the form of a resin, Rf: 0.43 (silica gel; toluene/acetone 7:3).

EXAMPLE 5

3-(3,4-Dimethoxyphenyl)-3-(4-imidazol-1-yl-phenyl)-acrylic acid morpholide (a) 3,4-Dimethoxy-4'-(imidazol-1-yl)-benzophenone 3,4-Dimethoxy-4'-fluorobenzophenone (5.2 g) and sodium imidazole (1.8 g) were heated at 100° C. for 4 hours in dimethylformamide (20 ml) and then the mixture was poured into water. The oil which precipitated was separated and triturated into crystals with water. The product was recrystallized from ethanol.

Yield: 4.3 g of the title compound in the form of crystals, m.p. 149°–151° C.

(b)
3-(3,4-Dimethoxyphenyl-3-(4-imidazol-1-yl-phenyl)acrylic acid morpholide

Diethylphosphonoacetic acid morpholide (4.5 g) was added, while stirring, to a suspension of sodium hydride (80%, 0.5 g) in tetrahydrofuran (30 ml), and the mixture was stirred for another hour at room temperature, 3,4-dimethoxy-4′-(imidazol-1-yl)-benzophenone (4.0 g) was added, and the mixture was boiled for 2 hours.

After the solvent had been distilled off, the residue was extracted with water/ethyl acetate, the organic phase was separated and evaporated and the residue was purified on silica gel with toluene/acetone (7:3).

Yield: 3.0 g of the title compound in the form of a colorless hard resin, Rf: 0.18 (silica gel, toluene/acetone 7:3).

EXAMPLE 6

3-(3,4-Dimethoxyphenyl)-3-[4-(3-phenylureido)-phenyl]-acrylic acid morpholide 3-(3,4-Dimethoxyphenyl)-3-(4-aminophenyl)-acrylic acid morpholide (2.2 g) was boiled for 2 hours together with phenylisocyanate (0.72 g) in toluene (40 ml).

The title compound was precipitated from the reaction mixture by adding gasoline and was then recrystallized from ethanol.

Yield: 2.0 g of the title compound in the form of colorless crystals, m.p. 215°–220° C. (decomp.).

EXAMPLE 7

3-(3,4-Dimethoxyphenyl)-3-(4-phenylazophenyl)-acrylic acid morpholide 3-(3,4-Dimethoxyphenyl)-3-(4-aminophenyl)-acrylic acid morpholide (2.2 g) was dissolved in glacial acetic acid (30 ml) while gently hating. At room temperature, nitrosobenzene (0.7 g) was added dropwise to this solution which was then stirred for another hour. The mixture was then boiled for 3 hours, poured into water and extracted with ethyl acetate. The organic phase was evaporated, and the residue was purified on silica gel with toluene/acetone (95:5).

Yield: 1.4 g of the title compound in the form of a strongly orange-colored resin, Rf: 0.55 (silica gel, cyclohexane/acetone 1:1).

EXAMPLE 8

3-(3,4-Dimethoxyphenyl)-3-[4-(4-chlorobenzoylamino)-phenyl]acrylic acid morpholide 3-Chlorobenzoyl chloride (3.5 g) was added dropwise to a suspension of 3-(3,4-dimethoxyphenyl)-3-(4-aminophenyl)acrylic acid morpholide (7.4 g) in dichloroethane (30 ml) and pyridine (1.6 g). The mixture was allowed to stand for 12 hours at room temperature and was then boiled for 1 hour. After the reaction mixture had been evaporated, the residue was mixed with water twice and the supernatant liquid was decanted each time. The residue was then triturated with methanol to form crystals.

Yield: 9.0 g of the title compound in the form of crystals, m.p. 197°–207° C.

EXAMPLE 9

3-(3,4-Dimethoxyphenyl)-3-[4-(2,5-dimethyl-pyrryl-1-yl)phenyl]-acrylic acid morpholide 3-(3,4-Dimethoxyphenyl)-3-(4-aminophenyl)-acrylic acid morpholide (5.0 g) was boiled for 3 hours with 2,5-hexanedione (10 ml).

Upon adding gasoline, a greasy mass was precipitated from the clear brown solution, and when triturated with diisopropyl ether this mass crystallized.

The product was purified by recrystallization from diisopropyl ether.

Yield: 3.3 g of the title compound in the form of beige crystals, m.p. 143°–145° C.

EXAMPLE 10

3-(3,4-Dimethoxyphenyl)-3 [4-(3-p-toluene-sulphonyl-ureido)phenyl]acrylic acid morpholide 3-(3,4-Dimethoxyphenyl)-3-(4-aminophenyl)acrylic acid morpholide (3.7 g) was boiled for 40 minutes together with p-toluenesulfonyl isocyanate (2.0 g) in toluene (40 ml).

After cooling, the precipitated product was suction-filtered off and recrystallized from methanol.

Yield: 2.3 g of the title compound in the form of colorless crystals, m.p. 220°–225° C.

EXAMPLE 11

3-(4-Ethoxycarbonylmethoxy-3-methyl-phenyl)-3-phenylacrylic acid morpholide 3-(4-Hydroxy-3-methylphenyl)3-phenylacrylic acid morpholide (8.1 g) was added to a solution of sodium ethoxide in ethanol (prepared from 077 g of sodium and 60 ml of ethanol), then ethyl chloracetate (3.8 g) was added dropwise, and the resulting mixture was boiled for 2 hours. After the solvent was evaporated, the residue was extracted with toluene/sodium hydroxide.

The product was isolated from the organic phase in the form of a resin after evaporation of the solvent.

Yield: 5.8 g of the title compound in the form of a resin, Rf: 0.475 (silica gel, toluene/acetone 7:3).

EXAMPLE 12

3-(3-Methyl-4-methylaminocarbonyloxyphenyl)-3-phenyl-acrylic acid morpholide

Methyl isocyanate (2.0 g) was added to a solution of 3(4-hydroxy-3-methylphenyl)-3-phenylacrylic acid morpholide (9.7 g) in toluene (50 ml) and triethylamine (1 ml) at 40° C. After 1 hour the mixture was extracted with water and sodium hydroxide, and the organic phase was evaporated.

The residue was purified on silica gel with toluene/acetone (7:3).

Yield: 6 g of the title compound in the form of a yellow resin, Rf: 0.3 (silica gel, toluene/acetone (7:3).

EXAMPLE 13

3-(3-Methyl-4-dimethylaminocarbonyloxyphenyl)-3-phenylacrylic acid morpholide

Analogous to Example 11, the title compound was obtained in the form of a resin, Rf: 0.4 (silica gel, toluene/acetone 7:3), starting from 3-(3-methyl-4-hydroxyphenyl)-3-phenylacrylic acid morpholide and N,N-dimethylcarbonyl chloride.

EXAMPLE 14

3-(3-Methyl-4-dimethylaminosulphonyloxyphenyl)-3-phenylacrylic acid morpholide Analogous to Example 11, the title compound was obtained in the form of crystals, m.p. 108° C. starting from 3-(3-methyl-4-hydroxyphenyl)-3-phenylacrylic acid morpholide and N,N-dimethylamidosulphonic acid chloride.

EXAMPLE 15

0,0-Diethyl-0-[2-methyl-4-(2-morpholinocarbonyl)-1-phenylvinylene)-phenyl]-phosphoric acid ester Analogous to Example 11, the title compound was obtained in the form of an oil, Rf: 0.24 (silica gel, toluene/acetone 7:3), starting from 3-(3-methyl-4-hydroxyphenyl)-3-phenylacrylic acid morpholide and 0,0-diethylphosphoric acid chloride.

EXAMPLE 16

3-(4-Benzyloxy-3-methylpheny)-3-phenylacrylic acid morpholide

Analogous to Example 11, the title compound was obtained as a brownish resin, Rf: 0.56 (silica gel, toluene/acetone 7:3), starting from 3-(4-hydroxy-3-methylphenyl)3-phenylacrylic acid morpholide.

EXAMPLE 17

3-(3-Methyl-4-trimethylsilyloxyphenyl)-3-phenylacrylic acid morpholide

Analogous to Example 11, the title compound was obtained as a resin, Rf: 0.59 (silica gel, toluene/acetone 7:3), starting from triethylchlorosilane and 3-(3-methyl-4-hydroxy- phenyl)-3-phenylacrylic acid morpholide.

EXAMPLE 18

3-(3-Methyl-4-methylsulfonyloxyphenyl)-3-phenylacrylic acid morpholide

Analogous to Example 11, the title compound was obtained as a resin, Rf: 0.73 (silica gel, toluene/acetone 3:7), starting from methanesulfonic chloride and 3-(3-methyl-4- hydroxyphenyl)-3-phenyl-acrylic acid morpholide.

EXAMPLE 19

3-[4-(4-Chlorosulfinyl)-phenyl]-3-(3,4-dimethoxyphenyl)acrylic acid morpholide Diethylphosphonoacetic acid morpholide (3.98 g) was added, while stirring, to a suspension of sodium hydride (80%, 0.45 g) in tetrahydrofuran (20 ml), and the mixture was stirred for another hour at room temperature, yielding a clear solution. A solution of 4-(4-chlorophenylsulfinyl)-3',4'-dimethoxybenzophenone (4.8 g) in tetrahydrofuran (10 ml) was then added to the clear solution, and the mixture was boiled for one hour.

The reaction mixture was then evaporated, and the residue was extracted with toluene/water.

The organic phase was evaporated, and the residue was purified on silica gel with toluene/acetone. Yield: 4.2 g of the title compound in the form of an oil, Rf: 0.28 (silica gel, toluene/acetone 7:3).

EXAMPLE 20

(1) 3-(Biphenyl-4-yl)-3-(3,4-dimethoxyphenyl)-acrylic acid morpholide (a) 3,4-Dimethoxy-4'-phenyl-benzophenone 300 g of veratrole was added dropwise over a period of 30 minutes to a suspension of 300 g of aluminum chloride in 300 ml of methylene chloride, taking care that the internal temperature did not exceed 30° C. Then, 450 g of biphenyl-4-carboxylic acid chloride were added in portions over a period of 30 minutes, while stirring and cooling (internal temperature 20°-25° C.). The resulting mixture was stirred for 4 hours at room temperature and was then poured into a mixture of 2 kg of ice/500 ml of concentrated hydrochloric acid. After the organic phase had been separated, the aqueous phase was extracted twice more with methylene chloride.

The combined organic phases were washed with acid, water and lye, then dried and evaporated. The residue was stirred with gasoline (85°-110° C., 11). 560 g of the title compound were isolated in the form of yellowish crystals (85% of theory).

(b) 3-(Biphenyl-4-yl)-3-(3,4-dimethoxyphenyl)-acrylic acid 11.5 g of triethylphosphonoacetate were added dropwise to a suspension of 1.6 g of NaH in 50 ml of 1,2-dimethoxyethane, while stirring and cooling on an ice bath. When a clear solution ha been obtained, 15 g of 3,4-dimethoxy -4'-phenylbenzophenone were added, and the mixture was heated at 100° C. for 5 hours. The precipitate was filtered off, and the filtrate was evaporated and taken up in toluene/water. The organic phase was washed once again with water, dried and evaporated. 17.4 g of a residue were boiled for 2.5 hours with aqueous methanolic KOH, and the solution was evaporated. The resulting potassium salt of the title compound was dissolved in water and precipitated as a resin by the addition of hydrochloric acid.

The title compound was obtained in crystalline form from the aqueous precipitate by trituration.

9.4 g of the title compound were isolated in the form of crystals, m.p. 178°-184° C., (decomp).

(c) 3-(Biphenyl-4-yl)-3-(3,4-dimethoxyphenyl)acrylic acid morpholide 4.7 g of carbonyldiimidazole were added in portions to a solution of 9.4 g of 3-(biphenyl-4-yl)-3-(3,4-dimethoxyphenyl)acrylic acid in 50 ml of anhydrous tetrahydrofuran. After the evolution of $CO_2$ had subsided, 2.5 g of morpholine were added, and the mixture was boiled for 1 hour. After evaporation, the residue was taken up in toluene/water, and the aqueous phase was discarded. The organic phase was washed once more with water, then dried and evaporated. The crude title compound was isolated with a yield of 10.5 g. The crude product was purified on silica gel with toluene/acetone (9:1). 6.2 g of the title compound were obtained in the form of a yellow resin, Rf: 0.56 ]l (silica gel, toluene/ acetone 7:3).

After recrystallization from methanol the title compound was obtained in crystalline form (m.p. 120°-128° C., sintering from 115° C.).

d) Synthesis of
3-(biphenyl-4-yl)-3-(3,4-dimethoxy-phenyl)acrylic acid morpholide from
3,4-dimethoxy-4'-phenyl-benzophenone and diethylphosphonoacetic acid morpholide 530 g of diethylphosphonoacetic acid morpholide were added dropwise over a period of 45 minutes to a suspension of sodium hydride (96 g of a 50% dispersion) in 3000 ml of tetrahydrofuran, taking care that the internal temperature did not exceed 45° C., and the mixture was allowed to react until the evolution of hydrogen had ceased. Then 566 g of 3,4-dimethoxy-4'-phenyl-benzophenone were added, and the mixture was boiled for 4 hours. After cooling to room temperature, 500 ml of water were added, the tetrahydrofuran was removed in water aspirator vacuum, and the residue was mixed with 500 ml of water and 200 ml of ethyl acetate. After the aqueous phase had been separated and re-extracted once more with ethyl acetate (500 ml), the combined organic phases were washed, dried and evaporated.

645 g (83.4%) of the title compound were isolated as a light brown mass which hardened into a glassy substance with an Rf of 0.56 (silica gel, toluene/acetone 7:3).

The following compounds were prepared analogously:
(2) 3-(Biphenyl-4-yl)-3-(3-methyl-4-methoxyphenyl)-acrylic acid morpholide
(3) 3-(Biphenyl-4-yl)-3-(3-bromo-4-methoxyphenyl)-acrylic acid morpholide
(4) 3-(Biphenyl-4-yl)-3-(3-chloro-4-methoxyphenyl)-acrylic acid morpholide
(5) 3-(Biphenyl-4-yl)-3-(4-methyl-3-methoxyphenyl)-acrylic acid morpholide
(6) 3-(Biphenyl-4-yl)-3-(3-bromo-4-dimethoxyphenyl)-acrylic acid morpholide
(7) 3-(Biphenyl-4-yl)-3-(3-ethyl-4-methoxyphenyl)-acrylic acid morpholide
(8) 3-(Biphenyl-4-yl)-3-(3-ethoxy-4-methoxyphenyl)-acrylic acid morpholide
(9) 3-(4-Amino-3,5-dichlorophenyl)-3-(biphenyl-4-yl)-acrylic acid morpholide
(10) 3-(4-Amino-3-methylphenyl)-3-(biphenyl-4-yl)-acrylic acid morpholide
(11) 3-(3-Amino-4-methoxyphenyl)-3-(biphenyl-4-yl)-acrylic acid morpholide
(12) 3-(3-Acetamido-4-methoxyphenyl)-3-(biphenyl-4-yl)-acrylic acid morpholide
(13) 3-(Biphenyl-4-yl)-3-(3-n-propyl-4-methoxyphenyl)-acrylic acid morpholide
(14) 3-(Biphenyl-4-yl)-3-(3,5-dichlorophenyl)-acrylic acid morpholide
(15) 3-(Biphenyl4-yl)-3-(3-methylthiomethyl-4-methoxyphenyl)acrylic acid morpholide
(16) 3-(4-Amino-3-bromophenyl)-3-(biphenyl-4-yl)-acrylic acid morpholide
(17) 3-(Biphenyl-4-yl)-3-(3,5-dimethylphenyl)-acrylic acid morpholide

EXAMPLE 21

E-3-(Biphenyl-4-yl)-3-(3,4-dimethoxyphenyl)acrylic acid morpholide 4.4 g (15 mmols) of E-4-phenylcinnamic acid morpholide, 4.35 g (16.5 mmols) of 4-iodoveratrole, and 315 mg (0.15 mmols) of 5% palladium-on-activated charcoal were refluxed for 8 hours with 7.5 ml of triethylamine and 10 ml of dimethylformamide. While still hot, the resulting solution was mixed with 20 ml of toluene and filtered, and the filtrate was extracted twice with water. After drying, the solution was separated using a column with 50 g of silica gel. Elution was carried out with toluene and a toluene/acetone mixture 95:5, 90:10, 80:20. The fractions containing the substance of Rf=0.56 (toluene/acetone 70:30) were evaporated in vacuo, and the residual viscous oil was recrystallized from methanol/diisopropyl ether.

Yield: 4.3 g (69%) of the title compound in the form of crystals, m.p. 127°–128° C.

'H-NRR spectroscopy showed no Z compound.

EXAMPLE 22 z-3-(Biphenyl-4-yl)-3-(3,4-dimethoxyphenyl)-acrylic acid morpholide

Analogous to Example 21, the title compound was prepared starting from 3,4-dimethoxycinnamic acid morpholide and 4-bromo-biphenyl.

EXAMPLE 23 z-3-(4-Benzolphenyl)-3-(3,4-dimethoxyphenyl)-acrylic acid morpholide 5.5 g (20 mmols) of 3,4-dimethoxycinnamic acid morpholide, 5.7 g (22 mmols) of 4-bromobenzophenone, 45 mg (0.2 mmols) of palldium-II-acetate and 122 mg (0.4 mmols) of tri-o-tolyphosphine were refluxed with 10 ml of triethylamine and 10 m of dimethylformamide for 15 hours. After cooling, the mixture was extracted with toluene/water, and the organic phase was washed again with water, dried and purified over a column with 60 g of silica gel. Elution was carried out with toluene and a 90:10 toluene-acetone mixture. The fractions containing the substance with Rf=0.34 (toluene/acetone 70:30) were evaporated in vacuo.

Yield: 4.0 g (44%) of the title compound with an E/Z ratio of 10/90.

EXAMPLE 24

E-3(4-Benzoylphenyl)-3-(3,4-dimethoxyphenyl)acrylic acid morpholide

This compound was obtained analogous to Example 23 by reacting 4-benzoylcinnamic acid morpholide and 4-bromoveratrole.

EXAMPLE 25 z-3-(3,4-Dimethoxyphenyl)-3-(4-hydroxyphenyl)acrylic acid morpholide

This compound was prepared in analogy to the preceding Examples by reacting 3,4-dimethoxycinnamic acid morpholide and 4-iodophenol.

EXAMPLE 26 z-3-(4-Cyanomethylphenyl)-3-(3,4-diethoxyphenyl)acrylic acid morpholide

This compound (Rf=0.32, silica gel, toluene/acetone=7:3) was prepared in analogy to the preceding Examples from 3,4-dimethoxycinnamic acid morpholide and 4-bromophenylacetonitrile.

EXAMPLE 27

E-3-(4-Cyanomethylphenyl)-3-(3,4-dimethoxyphenyl)acrylic acid morpholide

This compound was prepared in analogy to the preceding Examples from 4-cyanomethylcinnamic acid morpholide and 4bromoveratrole.

EXAMPLE 28 z-3-(4-Carboxymethylphenyl)-3-(3,4-dimethoxyphenyl-)acrylic acid morpholide

This compound was obtained in analogy to the preceding Examples in the form of crystals, m.p. 192°–194° C., from 3,4dimethoxycinnamic acid morpholide and (4-bromophenyl)-acetic acid.

EXAMPLE 29 z-3-(3,4-Dimethoxyphenyl)-3-(4-formylphenyl)acrylic acid morpholide

This compound was obtained in analogy to the preceding Examples from 3,4-di-methoxycinnamic acid morpholide and 4bromobenzaldehyde.

EXAMPLE 30 z-3-(3,4-Dimethoxyphenyl)-3-[4-(1,3-dioxolan-2-yl)-phenyl]acrylic acid morpholide ·

This compound was obtained in analogy to the preceding Examples from 3,4-dimethoxycinnamic acid morpholide and 2-(4-bromophenyl)-1,3-dioxolane.

EXAMPLE 31

E-3-(3,4-Dimethoxyphenyl)-3-[4-(4-n-propyl-1,3-dioxan-2-yl)phenyl]-acrylic acid morpholide This compound was obtained in analogy to the preceding Examples from 4-(4-n-propyl-1,3-dioxolan-2-yl)-cinnamic acid morpholide and 4-bromoveratrole.

EXAMPLE 32 z-3-(3,4-Dimethoxyphenyl-3-[4-(4-n-propyl-1,3-dioxan-2-yl)phenyl]acrylic acid morpholide This compound was obtained in analogy to the preceding Examples from 2-(4-bromophenyl)-4-n-propyl-1,3-dioxolane and 3,4=dimethoxycinnamic acid morpholide.

EXAMPLE 33

E-3-(3,4-Dimethoxyphenyl)-3-[4-(1,3-dithian-2-yl)-phenyl]acrylic acid morpholide This compound was obtained in analogy to the preceding Examples from 4-(1,3-dithioxan-2-yl)-cinnamic acid morpholide and 4-bromoveratrole.

EXAMPLE 34

3-(3,4-Dimethoxyphenyl)-3-[4-(1,2-dichlorovinyloxy]-phenyl)acrylic acid morpholide 5.5 g of 3-(3,4-dimethoxyphenyl)-3-(4-hydroxyphenyl)acrylic acid morpholide were dissolved in 40 ml of an equivalent sodium alkoxide solution, the solution was evaporated, and the residue was dissolved in 40 ml of dimethylformamide. At 60° C., 2.2 g of trichloroethylene in 5 ml of dimethylformamide were added dropwise to this solution. The mixture was stirred for 6 hours at 80° C. and then evaporated in vacuo. The residue was taken up in toluene/water and shaken. After the toluene phase had been dried and evaporated, 5.2 g of the title compound were obtained. Rf value: 0.77 (toluene/acetone 3:7).

EXAMPLE 35

3-(3,4-Dimethoxyphenyl)-3-(4-nitrophenyl)-acrylic acid morpholide 10.3 g of sodium hydride with 20% paraffin oil (0.343 mol) were suspended in 350 ml of tetrahydrofuran while stirring, and 75 g of diethylphosphonoacetic acid morpholide (0.0283 mol) were added dropwise to the suspension over a period of 20 minutes while cooling with ice (internal temperature 25° C.). The mixture was allowed to react for an hour during which a clear solution was formed. 70 g (0.244 mol) of 3,4-dimethoxy-4'-nitrobenzophenone were added to this solution all at once, and the mixture was refluxed for 2 hour while stirring. The solution was then evaporated in vacuo in a rotary evaporator at 60° C., and the residue was dissolved in methylene chloride/water. The organic phase was washed with water, dried over sodium sulfate and evaporated in vacuo at 60° C. The residue was triturated with 300 ml of hot methanol. 70.4 g of the title compound were obtained in the form of a faintly beige powder (73% of theory), m.p. 149°–163° C.

EXAMPLE 36

3-(3,4-Dimethoxyphenyl)-3-(4-aminophenyl)acetic acid morpholide 155 g of iron powder (2.77 mol) were mixed with 4 ml of glacial acetic acid in 700 ml of water. The mixture was heated to 75° C. while stirring, and 70 g of 3-(3,4-dimethoxyphenyl)-3-(4-nitrophenyl)acrylic acid morpholide (0.18 mol) were added in portions over a period of 10 minutes. The resulting mixture was stirred for 75 minutes on a steam bath (internal temperature 90° C.) and was then allowed to cool to room temperature. After suction-filtering off the precipitate was boiled with 500 ml of tetrahydrofuran, suction-filtered off again, and the filtrate was evaporated in vacuo at 60° C. The residue was digested with 100 ml of cold methanol and then suction-filtered until dry. 49 g of pure substance were obtained (a further 8 g from the mother liquor). The title compound (57 g of a pale yellow powder, 87% of theory) had a m.p. of 169°–176° C.

EXAMPLE 37

3-(3,4-Dimethoxyphenyl)-3-(4-hydroxyphenyl)acrylic acid morpholide 56 g (0.152 mol) of the amino compound obtained in the preceding example were dissolved in 60 ml of hot semiconcentrated hydrochloric acid while stirring, and the solution was then cooled to −5° C. Over a period of 25 minutes, a solution of 11 g of sodium nitrite in 50 ml of water was added dropwise. The mixture was stirred or 20 minutes more at 0° C. and was then slowly heated to 90° C. in the course of an hour. At this temperature it was stirred for another 1.5 hours. The aqueous phase was decanted, the residue was dissolved in hot dilute sodium hydroxide, mixed with activated charcoal and filtered while hot. The cooled filtrate was acidified with concentrated hydrochloric acid while cooling with ice, then stirred for some time, and the precipitate was suction-filtered off. 26 g of a beige powder were obtained (53% of theory), m.p. 105°–120° C., Rf=0.54 (toluene-/acetone 1:1).

EXAMPLE 38

3-(3,4-Dimethoxyphenyl)-3-[4-(4,6-dichloro-1,3,5-triazin-2-yloxy)phenyl]acrylic acid morpholide A phenoxide solution prepared from 4.1 g of the phenol obtained in the preceding example (0.011 mol), 0.5 g of 85% sodium hydroxide and 5 ml of water was added dropwise, at room temperature to a solution of 1.9 g (0.01 mol) of cyanuryl chloride in 12 ml of chloroform. The mixture was stirred for 1.5 hours at 50° C., diluted with 50 ml of chloroform, and the organic phase was separated, washed with cold dilute sodium hydroxide and with a common salt solution, dried with sodium sulfate and evaporated in vacuo at 60° C. The crude product (6.5 g was purified on a silica gel column (toluene/acetone 1:1). The title compound was obtained with a yield of 3.1 g (60% of theory), m.p. 90°-100° C., Rf=0.60 (toluene/acetone 1:1).

EXAMPLE 39

3-(3,4-Dimethoxyphenyl)-3-[4-(2-styryl)-phenyl]acrylic acid morpholide 13 g of 3-(3,4-dimethoxyphenyl)-3-(4-bromophenyl)acrylic acid morpholide (0.03 mol) were dissolved in 60 ml of dimethylformamide/triethylamine 1:1, then 4.2 g of styrene (0.04 mol) and 68 mg of palladium-(II)-acetate (0.3 mmol) and 183 mg of tri-(o-tolyl)-phosphine (0.6 mmol) were added, and the resulting mixture was refluxed for 12 hours. After cooling to room temperature, 100 ml of toluene were added, the mixture was suction-filtered, add the filtrate was washed with water, dilute hydrochloric acid, again with water and finally with saturated common salt solution. The organic phase was dried over sodium sulfate and then evaporated in vacuo at 60° C. The crude product (15 g) was purified by chromatography (silica gel column; eluant: toluene/acetone 1:1). By concentrating the solution in vacuo at 60° C., 10.8 g of an orange oil were obtained, 79% of theory. Rf=0.31 (touene/acetone 7:3).

EXAMPLE 40

3-(3,4-Dimethoxyphenyl)-3-[4-(1-carboxy-1-styryl)-phenyl]acrylic acid morpholide 4.3 g of 3-(3,4-dimethoxyphenyl)-3-(4-bromophenyl)acrylic acid morpholide (0.01 mol) and 1.95 g of cinnamic acid (0.013 mol) were dissolved in 20 ml of triethylamine and 10 ml of dimethyformamide, then 23 mg of palladium-(II)acetate (0.1 mmol) and 61 mg of tri-(o-tolyl)-phosphine (0.2 mmol) were added to the solution, and the resulting mixture was refluxed for 16 hours. After cooling, the solvents were removed in vacuo at 60° C., and the residue was dissolved in 200 ml of ethyl acetate, acidified with 2N hydrochloric acid and suction-filtered. The organic phase was dried with sodium sulfate, evaporated in vacuo, and the residue was purified on a silica gel column, acetone/ethanol 1:1 by chromatography. 1.8 g (36% of theory) of a solidifying compound were obtained from the solution. Rf=0.23 (toluene/acetone 7:1).

EXAMPLE 41

3-(3,4-Dimethoxypenyl)-3-[4-(1-styryl)-phenyl]-acrylic acid morpholide 4.6 g of the carboxylic acid obtained in Example 40 (9.2 mmols) were refluxed for 5 hours, while stirring, in a mixture of 30 ml of dioxane and 30 ml of concentrated hydrochloric acid in order to decarboxylate it. The solution was evaporated in vacuo at 60° C., the residue was taken up in toluene and the solution was evaporated to dryness. The residue was purified by chromatography on a silica gel column with toluene/acetone 7:3. An oil was obtained from the solution, and this oil slowly crystallized. Yield: 3.3 g (79% of theory), m.p. 115°-124° C. (from diisopropyl ether, Rf=0.45 (toluene/acetone 7:3).

Using the methods described above, the following compounds of the formula

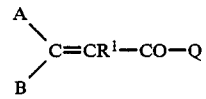

shown in the following tables were also synthesized.

Those compounds which exist as oils or resins are characterized by their Rf value. The Rf value was determined by thin-layer chromatography on silica gel plates with the following eluant mixtures:
(1) toluene/acetone 7:3
(2) toluene/acetone 3:7
(3) Ethyl acetate.

TABLE I

| No. | R¹ | A | B | Q | Physical Data |
|---|---|---|---|---|---|
| 1 | H | 3-CH₃-4-CH₃O—C₆H₃ | 4-C₆H₅—O—C₆H₄ | morpholino | Rf: 0.54¹ |
| 2 | H | C₆H₅ | 3-CH₃-4-(C₂H₅O—CO—CH(CH₃)—O)—C₆H₃ | morpholino | Rf: 0.52¹ |
| 3 | H | C₆H₅ | 3-CH₃-4-(C₂H₅—O—CO—CH₂—O)—C₆H₃ | morpholino | Rf: 0.48¹ |
| 4 | H | 3,4-(CH₃O)₂—C₆H₃ | 4-(n-C₆H₁₃)—C₆H₄ | morpholino | Rf: 0.45¹ |
| 5 | H | 3,4-(CH₃O)₂—C₆H₃ | 4-(n-C₅H₁₁)—C₆H₄ | morpholino | Rf: 0.47¹ |
| 6 | H | 3,4-(CH₃O)₂—C₆H₃ | 4-(n-C₁₂H₂₅)—C₆H₄ | morpholino | Rf: 0.48¹ |
| 7 | H | 3,4-(CH₃O)₂—C₆H₅ | 4-(4-NO₂—C₆H₄)—C₆H₄ | morpholino | Rf: 0.36¹ |
| 8 | H | C₆H₅ | 4-CH₃O-3-[(EtO)₂POCH₂]—C₆H₃ | morpholino | Rf: 0.11¹ |
| 9 | H | C₆H₅ | 4-CH₃O-3-(NC—CH₂)—C₆H₃ | morpholino | Rf: 0.42¹ |
| 10 | H | C₆H₅ | 4-CH₃O-3-(Imidazol-1-yl-methyl)C₆H₃ | morpholino | Rf: 0.13² |
| 11 | H | C₆H₅ | 4-CH₃—O-3-(1,2,4-Triazol-1-yl-methyl)-C₆H₃ | morpholino | |
| 12 | H | C₆H₅ | 4-CH₃O-3-CH₃SCH₂—C₆H₃ | morpholino | m.p.: 105-120° |
| 13 | H | C₆H₅ | 4-NO₂—C₆H₄—O—C₆H₄ | morpholino | |
| 14 | H | 3,4-(CH₃O)₂—C₆H₃ | 4-C₅H₁₁—O—C₆H₄ | morpholino | Rf: 0.57³ |
| 15 | H | C₆H₅ | 4-CH₃O-3-[(CH₃)₂NCH₂]—C₆H₃ | morpholino | m.p.: 123-125° |
| 16 | H | C₆H₅ | 4-CH₃O-3-(C₆H₅—O—CH₂)—C₆H₃ | morpholino | Rf: 0.53¹ |
| 17 | H | 3,4-(CH₃O)₂—C₆H₃ | 4-[(CH₃)₂NSO₂]—C₆H₄ | morpholino | Rf: 0.26¹ |
| 18 | H | 3,4-(CH₃O)₂—C₆H₃ | 4-(1,2,4-Triazol-1-yl)-C₆H₄ | morpholino | m.p.: 145-146° |
| 19 | H | 3,4-(CH₃O)₂—C₆H₃ | 4-(4-Cl—C₆H₄—SO₂)—C₆H₄ | morpholino | m.p.: 173-175° |
| 20 | H | 3,4-(CH₃O)₂—C₆H₃ | 4-(4-Cl—C₆H₄O)C₆H₄ | morpholino | Rf: 0.41¹ |
| 21 | H | 3,4-(CH₃O)₂—C₆H₃ | 4-(C₆H₅—O—CH₂)C₆H₄ | morpholino | Rf: 0.42¹ |

TABLE I-continued

| No. | R[1] | A | B | Q | Physical Data |
|---|---|---|---|---|---|
| 22 | H | 3,4-(CH$_3$O)$_2$—C$_6$H$_3$ | 4-(C$_6$H$_5$—CH$_2$—O)C$_6$H$_4$ | morpholino | Rf: 0.42[1] |
| 23 | H | 3,4-(CH$_3$O)$_2$—C$_6$H$_5$ | 4-(4-CH$_3$—C$_6$H$_4$—O)C$_6$H$_4$ | morpholino | Rf: 0.45[1] |
| 24 | H | 3,4-(CH$_3$O)$_2$—C$_6$H$_3$ | 4-(C$_6$H$_5$—NH—CO—NH)—C$_6$H$_4$ | morpholino | m.p.: 215–220° |
| 25 | H | 3,4-(CH$_3$O)$_2$—C$_6$H$_3$ | 4-(4-C$_2$H$_5$—C$_6$H$_4$)—C$_6$H$_4$ | morpholino | m.p.: 65–67° |
| 26 | H | 3,4-(CH$_3$O)$_2$—C$_6$H$_3$ | 4-(HOCH$_2$CH$_2$NHCO)—C$_6$H$_4$ | morpholino | Rf: 0.15[1] |
| 27 | H | C$_6$H$_5$ | 4-CH$_3$O-3-H$_2$NCH$_2$—C$_6$H$_3$ | morpholino | Rf: 0.06[2] |
| 28 | H | 3,4-(CH$_3$O)$_2$—C$_6$H$_3$ | 1,2,3,4-Tetrahydronaphthalin-6-yl | morpholino | Rf: 0.41[1] |
| 29 | H | 3,4-(CH$_3$O)$_2$—C$_6$H$_3$ | 4-Pyrazol-1-yl-C$_6$H$_4$ | morpholino | Rf: 0.28[1] |
| 30 | H | C$_6$H$_5$ | 4-CH$_3$O-3-(Morpholin-4-yl-methyl)C$_6$H$_3$ | morpholino | Rf: 0.14[1] |
| 31 | H | C$_6$H$_5$ | 4-CH$_3$O-3-(2,6-dimethyl-morpholin-4-yl-methy)-C$_6$H$_3$ | morpholino | Rf: 0.28[1] |
| 32 | H | 3,4-(CH$_3$O)$_2$—C$_6$H$_3$ | Indan-5-yl | morpholino | Rf: 0.40[1] |
| 33 | H | 3,4-(CH$_3$O)$_2$—C$_6$H$_3$ | 4-(Morpholin-4-yl)-C$_6$H$_4$ | morpholino | Rf: 0.25[1] |
| 34 | H | 4-Cl—C$_6$H$_4$ | 4-(CH$_3$SO$_2$—O)—C$_6$H$_4$ | morpholino | Rf: 0.35[1] |
| 35 | H | C$_6$H$_5$ | 4-CH$_3$O-3-(4-Cl—C$_6$H$_4$—S—CH$_2$)C$_6$H$_3$ | morpholino | Rf: 0.56[1] |
| 36 | H | C$_6$H$_5$ | 3-CH$_3$-4-[(CH$_3$)$_3$SiCH$_2$O]—C$_6$H$_3$ | morpholino | Rf: 0.59[1] |
| 37 | H | 3,4-(CH$_3$O)$_2$C$_6$H$_3$ | 4-C$_6$H$_5$O—C$_6$H$_4$ | morpholino | Rf: 0.39[3] |
| 38 | H | 3,4-(CH$_3$O)$_2$C$_6$H$_3$ | Dibenzofuran-2-yl | morpholino |  |
| 39 | H | 3,4-(CH$_3$O)$_2$C$_6$H$_3$ | Fluoren-2-yl | morpholino | Rf: 0.44[1] |
| 40 | H | 3,4-(CH$_3$O)$_2$C$_6$H$_3$ | 4-(n-C$_4$H$_9$)—C$_6$H$_4$ | morpholino | Rf: 0.41[1] |
| 41 | H | 3,4-(CH$_3$O)$_2$C$_6$H$_3$ | 4-(sek—C$_4$H$_9$)—C$_6$H$_4$ | morpholino | Rf: 0.47[1] |
| 42 | H | 3,4-(CH$_3$O)$_2$C$_6$H$_3$ | 4-(iso—C$_4$H$_9$)—C$_6$H$_4$ | morpholino | Rf: 0.46[1] |
| 43 | H | 3,4-(CH$_3$O)$_2$C$_6$H$_3$ | 4-C$_6$H$_5$—C$_6$H$_4$ | morpholino | Rf: 0.56[1] |
| 44 | H | 3-Cl-4-CH$_3$O—C$_6$H$_3$ | 3-C$_6$H$_5$O—C$_6$H$_4$ | morpholino |  |
| 45 | H | 3-CH$_3$-4-CH$_3$O—C$_6$H$_3$ | 4-(2-Cl—C$_6$H$_4$O)—C$_6$H$_4$ | N(CH$_3$)$_2$ |  |
| 46 | H | 3-CH$_3$O-4-CH$_3$—C$_6$H$_3$ | 4-(2-C$_2$H$_5$O$_2$C—C$_6$H$_4$O)C$_6$H$_4$ | morpholino |  |
| 47 | H | 3-C$_2$H$_5$-4-CH$_3$O—C$_6$H$_3$ | 4-(3-Cl—C$_6$H$_4$O)C$_6$H$_4$ | morpholino |  |
| 48 | H | 3-Br-4-N(CH$_3$)$_2$—C$_6$H$_3$ | 4-(4-CH$_3$O—C$_6$H$_4$O)C$_6$H$_4$ | morpholino |  |
| 49 | H | 3-Br-4-N(CH$_3$)$_2$—C$_6$H$_3$ | 4-(4-CH$_3$O—C$_6$H$_4$O)C$_6$H$_4$ | morpholino |  |
| 50 | H | 3,5-Cl$_2$-4-NH$_2$—C$_6$H$_2$ | 4-(2-CH$_3$O—C$_6$H$_4$O)C$_6$H$_4$ | morpholino |  |
| 51 | CH$_3$ | 3,5-(CH$_3$)$_2$-4-CH$_3$OC$_6$H$_2$ | 4-(4-Br—C$_6$H$_4$)C$_6$H$_4$ | morpholino |  |
| 52 | H | 3-Br-4-CH$_3$OC$_6$H$_3$ | 3-Cl-4-(3-CH$_3$C$_6$H$_4$S)C$_6$H$_3$ | morpholino |  |
| 53 | H | 3,4-(CH$_3$)$_2$—C$_6$H$_3$ | 4-(4-CH$_3$—C$_6$H$_4$)—C$_6$H$_4$ | morpholino |  |
| 54 | H | 3-NH$_2$-4-CH$_3$OC$_6$H$_3$ | 4-(4-F—C$_6$H$_5$O)C$_6$H$_4$ | morpholino |  |
| 55 | H | 3-NH$_2$-4-CH$_3$—C$_6$H$_3$ | 4-C$_6$H$_5$S—C$_6$H$_4$ | morpholino |  |
| 56 | Br | 3-CH$_3$-4-C$_2$H$_5$OC$_6$H$_3$ | 4-(4-NH$_2$—C$_6$H$_4$)C$_6$H$_4$ | morpholino |  |
| 57 | H | 3-Cl-4-CH$_3$—OC$_6$H$_3$ | 4-(C$_3$H$_7$—C$_6$H$_4$)C$_6$H$_4$ | morpholino |  |
| 58 | H | 3-CH$_3$-4-CH$_3$OC$_6$H$_5$ | 4-(C$_4$H$_9$OC$_6$H$_4$O)—C$_6$H$_4$ | morpholino |  |
| 59 | H | 3-CH$_3$O-4-CH$_3$C$_6$H$_3$ | 4-C$_6$H$_5$O—C$_6$H$_4$ | morpholino |  |
| 60 | H | 3-Br-4-NHCH$_3$C$_6$H$_3$ | 4-(2-Cl—C$_6$H$_4$S)C$_6$H$_4$ | morpholino |  |
| 61 | H | 3,5-Cl$_2$-4-NH$_2$—C$_6$H$_2$ | 4-(3,4-(CH$_3$)$_2$—C$_6$H$_3$O)C$_6$H$_4$ | morpholino |  |
| 62 | H | 3-C$_2$H$_5$-4-CH$_3$OC$_6$H$_3$ | 4-(2-ClC$_6$H$_4$)—C$_6$H$_4$ | morpholino |  |
| 63 | H | 3-Cl-4-CH$_3$OC$_6$H$_3$ | 4-(2,3-Cl$_2$C$_6$H$_3$)—C$_6$H$_4$ | morpholino |  |
| 64 | H | 3-CH$_3$-4-CH$_3$O—C$_6$H$_3$ | 4-(3-Cl—C$_6$H$_4$)—C$_6$H$_4$ | morpholino |  |
| 65 | H | 3-Br-4-CH$_3$O—C$_6$H$_3$ | 4-(C$_2$H$_5$OC$_6$H$_4$)C$_6$H$_4$ | morpholino |  |
| 66 | H | 3,4-(CH$_3$O)$_2$—C$_6$H$_3$ | 4-(CH$_3$OCO—C$_6$H$_4$)C$_6$H$_4$ | morpholino |  |
| 67 | H | 3,4-(CH$_3$)$_2$—C$_6$H$_3$ | 4-(4-C$_2$H$_5$O—CO—C$_6$H$_4$O)C$_6$H$_4$ | morpholino |  |
| 68 | H | 3,4-(CH$_3$O)$_2$—C$_6$H$_3$ | 4-(1-Pyrryl)-C$_6$H$_4$ | morpholino | m.p.: 164–166° |
| 69 | H | 3,4-(CH$_3$O)$_2$—C$_6$H$_3$ | 4-(4-Cl—C$_6$H$_4$)—C$_6$H$_4$ | morpholino | Rf: 0.45[1] |
| 70 | H | 3,4-(CH$_3$O)$_2$—C$_6$H$_3$ | 4-(2,5-Dioxopyrrol-1-yl)-C$_6$H$_4$ | morpholino |  |
| 71 | H | 3-C$_2$H$_5$O-4-CH$_3$O—C$_6$H$_4$ | 4-(2,4-Cl$_2$—C$_6$H$_3$S)—C$_6$H$_4$ | N(CH$_3$)C$_2$H$_5$ |  |
| 72 | CH$_3$ | 3-Cl-4-CH$_3$O—C$_6$H$_3$ | 4-(4-Br—C$_6$H$_4$O)—C$_6$H$_4$ | N(CH$_3$)C$_3$H$_7$ |  |
| 73 | H | 3-Br-4-CH$_3$O—C$_6$H$_3$ | 3,4-Cl$_2$—C$_6$H$_3$C$_6$H$_4$ | 2-methyl-morpholino |  |
| 74 | CN | 3-CH$_3$-4-CH$_3$O—C$_6$H$_3$ | 1-Naphthoxy—C$_6$H$_4$ | morpholino |  |
| 75 | H | 3-CH$_3$O-4-CH$_3$C$_6$H$_3$ | 2-Naphthoxy—C$_6$H$_4$ | morpholino |  |
| 76 | H | 3,5-Cl$_2$-4-NH$_2$—C$_6$H$_2$ | 4-(4-CH$_3$—C$_6$H$_4$—S)—C$_6$H$_4$ | morpholino |  |
| 77 | Cl | 3-C$_2$H$_5$-4-CH$_3$O—C$_6$H$_3$ | 4-C$_6$H$_5$NH—C$_6$H$_4$ | morpholino |  |
| 78 | Br | 3-C$_3$H$_7$-4-CH$_3$OC$_6$H$_3$ | 4-(1-Naphthylthio)-C$_6$H$_4$ | morpholino |  |
| 79 | H | 3-Br-4-(CH$_3$)$_2$N—C$_6$H$_3$ | 4-(4-ClC$_6$H$_4$CH$_2$O)—C$_6$H$_4$ | N(CH$_2$CH$_3$)$_2$ |  |
| 80 | H | 3,4-(CH$_3$)$_2$C$_6$H$_3$ | 4-(4-NO$_2$—C$_6$H$_4$CH$_2$O)—C$_6$H$_4$ | morpholino |  |
| 81 | H | 3-NH$_2$-4-CH$_3$OC$_6$H$_3$ | 4-(2,4-Cl$_2$—C$_6$H$_3$O)—C$_6$H$_4$ | morpholino |  |
| 82 | H | 3-NHCOCH$_3$-4-CH$_3$O—C$_6$H$_3$ | 4-C$_6$H$_5$—CH$_2$S—C$_6$H$_4$ | morpholino |  |
| 83 | H | 3-NHCOCH$_3$-4-Cl—C$_6$H$_3$ | 4-(4-Cl—C$_6$H$_4$)—C$_6$H$_4$ | morpholino |  |
| 84 | H | 3,5-(CH$_3$)$_2$-4-CH$_3$O—C$_6$H$_2$ | 3-Cl-4-(2,4-(CH$_3$)$_2$—C$_6$H$_3$O)C$_6$H$_3$ | morpholino |  |
| 85 | H | 4-CH$_3$O—C$_6$H$_4$ | 4-(C$_6$H$_5$CH$_2$)—C$_6$H$_4$ | morpholino |  |
| 86 | H | 4-C$_2$H$_5$O—C$_6$H$_4$ | 4-C$_6$H$_5$—CH=CH—C$_6$H$_4$ | morpholino |  |
| 87 | CH$_3$ | 3-C$_2$H$_5$O-4-CH$_3$O—C$_6$H$_3$ | 4-(4-CN—C$_6$H$_4$O)—C$_6$H$_4$ | N(CH$_3$)(C$_4$H$_9$) |  |
| 88 | H | 3-Br-4-CH$_3$O—C$_6$H$_3$ | 4-(3-NO$_2$—C$_6$H$_4$O)—C$_6$H$_4$ | morpholino |  |

TABLE II

Compounds of the formula

[Structure: 3,4-dimethoxyphenyl group attached via C=CH-CO-N(morpholine) to a phenyl group bearing R⁷YX substituent]

| No. | —XYR⁷ | Physical Data |
|---|---|---|
| 1 | 4-n-OC₄H₉ | Rf = 0.43¹ |
| 2 | 4-n-C₃H₇ | Rf = 0.47¹ |
| 3 | 3-O-(4-Cl-phenyl) | Rf = 0.43¹ |
| 4 | 4-n-C₅H₁₁ | Rf = 0.47¹ |
| 5 | 4-N(CH₂—C₆H₅)(COCH₃) | Rf = 0.21¹ |
| 6 | 4-O-(4-Cl,3-CH₃-phenyl) | Rf = 0.47¹ |
| 7 | 4-O-(Cl-phenyl) | Rf = 0.41¹ |
| 8 | 4-OCH₂—CH=CH₂ | Rf = 0.69² |
| 9 | 4-OCCl=CHCl | Rf = 0.72² |
| 10 | 4-OCH₂—C≡CH | Rf = 0.65² |
| 11 | 4-(CH₂)₃—OCH₃ | Rf = 0.35¹ |
| 12 | 4-O-(4-CN-phenyl) | Rf = 0.40¹ |
| 13 | 4-O-(3-Cl-phenyl) | Rf = 0.40¹ |
| 14 | 4-OSO₂N(CH₃)₂ | Rf = 0.68² |
| 15 | 4-OCOC(CH₃)₃ | Rf = 0.72² |
| 16 | 4-O(CH₂)₃—OH | Rf = 0.51² |
| 17 | 4-OCF₂H | Rf = 0.38¹ |
| 18 | 4-NH—CO—(CH₂)₃—C₆H₅ | Rf = 0.38 (in methylenechloride/acetonitrile 1:1) |
| 19 | 4-OCH₂CF₃ | Rf = 0.38¹ |
| 20 | 4-(cyclohexyl-n-C₂H₅) | Rf = 0.52¹ |
| 21 | 4-(cyclohexyl-n-C₇H₁₅) | Rf = 0.55¹ |
| 22 | 4-OCH₂-(2,2-dichlorocyclopropyl) | Rf = 0.47 (toluene/acetone 1:1) |
| 23 | 4-COCH₃ | Rf = 0.31¹ |
| 24 | 4-N(piperidine) | Rf = 0.37¹ |
| 25 | 2-CO—C₆H₅ | Rf = 0.43¹ |
| 26 | 4-O-(6-chloro-2-ethylamino-pyrimidin-4-yl) | Rf = 0.40¹ |
| 27 | 3-CN | Rf = 0.40¹ |
| 28 | 4-SO₂NH—C₆H₅ | Rf = 0.29¹ |
| 29 | 4-CH₂—COOH | m.p.: 192–194° C. |
| 30 | 4-CN | Rf = 0.32¹ |
| 31 | 4-n-C₆H₁₃ | Rf = 0.45¹ |
| 32 | 4-n-C₇H₁₅ | Rf = 0.58¹ |
| 33 | 3-C₆H₅ | Rf = 0.42¹ |
| 34 | 4-OCH₂CF₂CF₂H | Rf = 0.35¹ |
| 35 | 4-CH=CH—COOH | Rf = 0.48 (toluene/ethanol 80:20) |
| 36 | 4-CH(O—CH₂—CH₂—O) (1,3-dioxolane) | Rf = 0.23¹ |
| 37 | 4-CH=CH—C₆H₅ | Rf = 0.31¹ |
| 38 | 4-CH=CH-(2-pyridyl) | Rf = 0.33¹ |
| 39 | 4-CH=CH-(3-pyridyl) | Rf = 0.33 (toluene/acetone 1:1) |

TABLE II-continued

Compounds of the formula $$\text{(3-CH}_3\text{O, 4-CH}_3\text{O-C}_6\text{H}_3\text{)C(=CH-CO-morpholine)(C}_6\text{H}_4\text{-XYR}^7\text{)}$$

| No. | —XYR⁷ | Physical Data |
|---|---|---|
| 40 | 4-cyclohexenyl | Rf = 0.45[1] |
| 41 | 4-CO-(3-pyridyl) | Rf = 0.16[1] |
| 42 | 4-CH$_2$OH | Rf = 0.21[1] |
| 43 | 4-CH=N-(morpholino) | Rf = 0.31[1] |
| 44 | 4-C(=CH-COOH)-C$_6$H$_5$ | Rf = 0.23[1] |
| 45 | 4-O-(4-F-C$_6$H$_4$) | Rf = 0.45[1] |
| 46 | 4-S-(4-Br-C$_6$H$_4$) | Rf = 0.46[1] |
| 47 | 4-O-[2-Cl-6-N(CH$_3$)$_2$-pyrimidin-4-yl] | Rf = 0.44[1] |
| 48 | 4-O-[2-Cl-6-NHCH(CH$_3$)$_2$-pyrimidin-4-yl] | Rf$_1$ = 0.44[1]<br>Rf$_2$ = 0.56<br>(E/Z mixture) |
| 49 | 4-CH$_2$O—CONH—C$_6$H$_5$ | Rf = 0.34[1] |
| 50 | 4-CH(1,3-dioxan-2-yl) | Rf = 0.36[1] |
| 51 | 4-C(=CH$_2$)—C$_6$H$_5$ | Rf = 0.45[1] |
| 52 | 4-O-(4,6-dichloro-1,3,5-triazin-2-yl) | Rf = 0.60[1]<br>(toluene/acetone 1:1) |
| 53 | 4-CH$_2$CO$_2$C$_2$H$_5$ | Rf = 0.33[1] |
| 54 | 4-CH=CH—CO$_2$C$_2$H$_5$ | Rf = 0.37[1] |
| 55 | 4-CH(1,3-dioxolan, 2-n-C$_3$H$_7$) | Rf = 0.40[1] |
| 56 | 4-NHCONHCH$_3$ | Rf = 0.20<br>(toluene/acetone 1:1) |
| 57 | 4-CON(CH$_3$)(C$_4$H$_9$-n) | Rf = 0.51[2] |
| 58 | 4-CO$_2$-n-C$_4$H$_9$ | Rf = 0.68[2] |
| 59 | 4-CONH-(4-Cl-C$_6$H$_4$) | m.p.: 228–230° C. |
| 60 | 4-CO—N(piperidino) | Rf = 0.23[1] |
| 61 | 4-CH=CH-n-C$_3$H$_7$ | Rf = 0.75<br>(toluene/acetone 1:1) |
| 62 | 4-CH=CH—CN | Rf = 0.39[1] |
| 63 | 4-(tetrahydropyran-2-yl-OH) | Rf$_1$ = 0.33<br>Rf$_2$ = 0.39<br>(toluene/acetone 1:1) |
| 64 | 4-O—CF$_2$CHClF | Rf = 0.40[1] |
| 65 | —CHOH—C$_6$H$_5$ | Rf = 0.34[1] |

TABLE III
Compounds of the formula
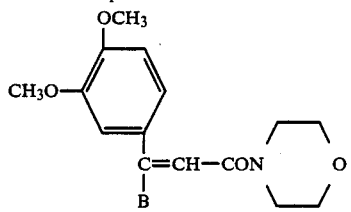
| No. | B | Physical Data |
|---|---|---|
| 1 | (dibenzofuran-CH2- type: 2-substituted with CH2 bridge and O) | Rf = 0.43< |
| 2 | pyrazine | Rf = 0.50 (toluene/ethanol 8:2) |
| 3 | benzofuran | m.p.: 147° C. |
| 4 | benzothiophene | m.p.: 150° C. |
| 5 | indole (NH) | Rf = 0.32[1] |
| 6 | biphenyl-CH2-CH2 | Rf = 0.37[1] |
| 7 | quinoline | Rf = 0.18[1] |
| 8 | indole (NH) | Rf = 0.30[1] |
| 9 | carbazole (N-C2H5) | Rf = 0.43[1] |

TABLE III-continued

Compounds of the formula

[Structure: 3,4-dimethoxyphenyl-C(B)=CH-CON(morpholine)]

| No. | B | Physical Data |
|---|---|---|
| 10 | N-methylpyrrole | Rf = 0.36[1] |

The novel compounds of the present invention, that is, those embraced by formula I above, have useful properties. More particularly, they exhibit very effective fungicidal activity against fungi, especially genuine mildew, phytopathogenic false mildews such as plasmopara and phytophthora, scab, grey mold and rust. Because of their very low phytotoxicity, the novel compounds may be used on virtually all useful and ornamental plants, for example on cereals such as corn, wheat, rye and oats, on rice, on tomatoes, cucumbers, beans, potatoes and beets, on grapevines and fruit trees, and on roses, carnations and chrysanthemums.

The novel compounds have a foliar as well as a systemic effect. Thus, with numerous compounds of the invention, when foliar treatment is carried out against plasmopora with a concentration of active ingredient between 20 and 100 ppm, all the fungi are killed.

For controlling phytophthora, concentrations of active ingredient of 100 ppm, sometimes less, are generally sufficient for adequate effects.

In many cases, it is advantageous to combine the compounds of the invention with known fungicidal substances. In some cases, the activity of the combinations is clearly greater than the sum of the activities of the components.

Combination partners:
Manganese ethylenebisdithiocarbamate (Maneb)
Manganese-zinc ethylenebisdithiocarbamate (Mancozeb)
Zinc ethylenebisdithiocarbamate (Zineb)
N-Trichloromethylthio-tetrahydrophthalimide (Captan)
N-Trichloromethylthiophthalimide (Folpet)
N-(1,1,2,2-Tetrachloroethylthio)tetrahydrophthalimide (Captafol)
2,3-Dicyano-1,4-dithiaanthraquinone (Dithianon)
Zinc-(N,N'-propylene-bisdithiocarbamate (Propineb)
Copper oxychloride
Sodium-4-dimethylaminobenzenediazoldiazosulphonate (Fenaminosulf)
Triphenyl tin acetate (Fentinacetat)
Triphenyl tin hydroxide (Fentinhydroxyd)
Iron dimethyldthiocarbamate (Ferbam)
N-(2-Furoyl)-N-(2,6-xylyl)-DL-alanine (Furalaxyl)
3-(Dimethylamino)propylcarbamate (Propamocarb)
N-Ethyl-N-(3-dimethylamino)thiocarbamate (Prothiocarb)
Tetramethylthiuramidesulfide (Thiram)
N-Dichlorofluoromethylhhio-N,N'-dimethyl-N-p-tolysulfamide (Tolylfluamid)
N-(2-Methoxyacetyl)-N-(2,6-xylyl)alanine (Metalaxyl)
Zinc dimethylthiocarbamate (Ziram)
N-Dichlorofluoromethylthio-N,N'-dimethyl-N-phenylsulfamide (Dichlorfluanid)
3-Trichloromethyl-5-ethoxy-1,2,4-thiadizole (Etridazol)
Tri[amine-zinc-ethylenebis(dithiocarbamate)]tetrahydro-1,2,4,7-dithiadiazicin-3,8-dithione polymer (Metiram)
Aluminotris-(O-ethylphoshate) (Phosethyl)
2-Cyano-N-(ethylcarbamoyl)-2-methyloximino)-acetamide (Cymoxanil)
N-(3-Chlorophenyl)-N-(tetrahydrofuran-2-on-3-yl)-cyclopropane carbonamite (Cyprofuran)
Tetrachloro-isophthalodinitrile (Chlorothalonil)
6-Methyl-2-oxo-1,3-dithio[4,5-b]-quinoxaline (Chinomethionat)
4-Cyclododeyyl-2,6-dimethylmorpholine (Dodemorph)
1-Dodecylguanidiniumacetate (Dodin)
Diisopropyl-5-nitroisophthalate (Nitrothal-isoproyyl)
2,4-Dichloro-α-(pyrmidin-5-yl)benzhydryl alcohol (Fenarimol)
1-(β-Allyloxy-2,4-dichlorophenethyl)imidazole (Imazalil)
3-(3,5-Dichlorophenyl)-N-isopropyl)-2,4-dioxoimidazolidine-1-carboxamide (Iprodion)
2,3-Dihydro-6-methyl-5-phenylcarbamoyl-1,4-oxythiine-4,4-dioxide (Oxycarboxin)
N-(3,5-Dichlorophenyl)-1,2-dimethylcyclopropane-1,2-dicarboximide (Procymidon)
6-Ethoxycarbony--5-methylpyrazolo[1,5-a]pyrimidin-2-yl-O,O-diethyl-phosphorothioate (Pyrazophos)
2-(Thiazol-4-yl-benzimidazole (Thiabendazol)
1-(4-Chlorophenoxy)3,3-dimethyl-1-(1,2,4-triazol-1-yl-2butanone (Triadimefon)
1-(4-Chlorophenoxy)3,3-dimethyl-1-(1,2,4-triazol-1-yl-butanol (Triadimenol)
3-(3,5-dichlorophenyl)-5-methyl-1-vinyloxazolidin-2,4dione (Vinclozolin)
Methylbenzimidazol-2-ylcarbamate (Carbendazin)
2,4,5-Trimethyl-N-phenyl-3-furancarboxamide (Methfuroxam)
β-([1,1-Biphenyl]-4-yl-oxy-α-(1,1-dimethylethyl)-1H-1,2,4-triazol-1-ethanol (Bitertanol)
2-(2-Furyl)benzimidazole (Fuberidazol)

5-Butyl-2-ethylamino-6-methylpyrimidin-4-ol (Ethirimol)
2-Methyl-3-furanlide (Fenfuram)
Bis-(8-guanidino-octyl)amine (Guazatin) 1
N-Cyclohexyl-N-methoxy-2,5-dimethylfuran-3-carboxylic acid amide (Furmecyclox)
2-Chloro-4'-fluoro-α-(pyrimidin-5-yl)benzhydryl alcohol (Nuarimol)
Phosphorous acid and the salts thereof
Methyl-1-(butylcarbamoyl)benzimidazolcarbamate (Benomyl)
O,O-Diethylphthalimidaophosphonathioate (Ditalimfos)
7-Bromo-5-chloroquinolin-8-acrylate (Halacrimat)
1-[2-(2,4-Dichlorophenyl)4-propyl-1,3-dioxolan-2-yl-methyl]1H-1,2,4-triazole (Propiconazol)
Dimethyl-4,4'-α-(o-phenylene) to (3-thioallophanate) (Thiopanatmethyl)
1,4-Bis(2,2,2-trichloro-1-flormamidoethyl)piperazine (Triforine)
2,2-Dimethyl-4-tridecylmorpholine (Tridemorph)
4-[3-]4-(1,1-Dimethyl-ethyl)phenyl[2-methyl]-propyl-2,6-(cis-dimethylmorpholine) (Fenpropimorph)
1-[2-(2,4-Dichlorophenyl)-4-ethyl-1,3-dioxolan-2-yl-methyl]1H-1,2,4-trizole (Etaconazol)
1-[1-(2,4-Chlorophenyl)-4,4-dimethyl-3-hydroxy-2-pentyl]1,2,4trizole (Diclobutrazol)
2,4-Dichloro-6-(2-chloroanilino)-1,3,5-triazine (Anilazin)
2-Iodo-N-phenylbenzamide (Benodanil)
2-sec.-butyl-4,6-dinitrophenyl-3-methylcrotonate (Binapacryl)
5-Butyl-2-(ethylamino)-6-methyl-4-pyrimidinyl-methylsulfonate (Buprimat)
2,4-Dinitro-6-octylphenylcrotinate (Dinocap)
5,6-Dihydro-2-methyl-1,4-oxathiin-3-carbanilide (Carboxin)
N-Propyl-N-[2,4,6-trichlorophenoxy)-2-ethyl]-imidazol-1-carbonamide (Prochloraz)

For use in plant protection, the novel compounds are processed in the usual way with inert excipients and/or carriers to produce conventional pesticidal forms, such as solutions, emulsifiable or soluble concentrates, wettable powders or dusting powders. If combinations containing other active ingredients are to be used, the substances may be mixed together in the form of common formulations or, for example, in the form of tank mixtures.

Before application, the concentrates are diluted with water, if necessary, to produce spray liquors with a content of active ingredient between about 0.001 and 1% by weight. If they are to be used in low volume or ultra-low volume formulations, the active ingredient may also be present in substantially larger amounts, up to about 20 or up to about 90% by weight, respectively.

Examples of formulations according to the invention:
1. Wettable powder
20 parts by weight of a compound of the formula I
20 parts by weight of kaolin
5 parts by weight of sodium sulfate
2 parts by weight f prepared chalk
9 parts by weight of calcium lignin sulfonate
1 part by weight of diisobutylnaphthalene sodium sulfonate
43 parts by weight of siliceous chalk The constituents are mixed and milled. For use, the composition is suspended in sufficient water to give a concentration of active ingredient of about 0.001 to 0.5% by weight.

2. Emulsifiable concentrate
15 parts by weight of a compound of the formula I
10 parts by weight of the triethylamine salt of dodecyl benzenesulfonic acid
75 parts by weight of dimethylformamide While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

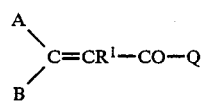

wherein
A is

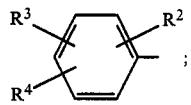

B is

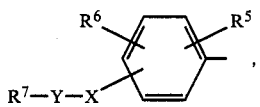

$R^1$ is hydrogen; halogen, cyano or optionally substituted $C_{1-4}$ alkyl;
Q is

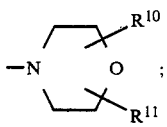

$R^2$, $R^3$, $R^4$, $R^5$ and $R^6$, which may be identical to or different from each other, are each hydrogen, halogen, nitro, cyano, carboxyl, hydroxyl, $C_{1-4}$ alkoxycarbonyl, $CONR^{10}R^{11}$, $NR^{10}R^{11}$, $NR^{10}$-$CO$-$R^{11}$, or the following optionally substituted groups: $C_{1-6}$ alkyl, $C_{1-4}$ alkoxy, $C_{1-4}$ alkyl-$S(O)_p$ (where p=0, 1 or 2), $C_{3-7}$ cycloalkyl, phenyl, phenoxy or phenyl-$S(O)_p$ (where p=0, 1 or 2);
$R^{10}$ and $R^{11}$, which may be identical to or different from each other, are each hydrogen, benzyl, phenyl or $C_{1-4}$ alkyl, or when not attached to the morpholine ring together they are —(CH$_2$)$_4$— or —(CH$_2$)$_5$—;
X-Y is —O— or —S(O)p— (where p=0, 1 or 2); and
$R^7$ is phenyl or substituted phenyl.

2. A compound of claim 1,
where A is 3,4-dimethoxyphenyl, 3-ethoxy-4-methoxyphenyl, 3-chloro-4-methoxyphenyl, 3-methyl-4-methoxyphenyl, 3-bromo-4-methoxyphenyl, 3- ethyl-4-methoxyphenyl, 3,4-dimethylphenyl or 3,5-dichloro-4-aminophenyl; and

B, Q and $R^1$ have the same meanings as in claim 1.

3. A compound of claim 2,
where A has the same meanings as in claim 2,
B and Q have the same meanings as in claim 1, and
$R^1$ is hydrogen.

4. A compound of claim 1, wherein A, Q and $R^1$ have the meanings defined in claim 1:
B is

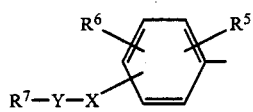

$R^5$, $R^6$ and $R^7$ have the meanings defined in claim 1, and —X-Y is oxygen or sulfur.

5. A compound of claim 4, where A, Q and $R^1$ have the meanings defined in claim 1, B is

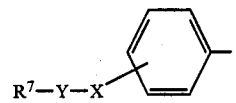

—X-Y is oxygen or sulfur;
$R^7$ is optionally substituted phenyl; and
$R^{10}$ and $R^{11}$ have the meaning defined in claim 1.

6. The compound of claim 1 which is 3-[4-(4-chlorophenoxy)-phenyl]-3-(3, acid morpholide.

7. A fungicidal agricultural compositions consisting essentially of an inert carrier and an effective fungicidal amount of a compound of claim 1.

8. The method of killing phytopathogenic fungi which comprises contacting said fungi with fungicidally effective amount of a compound of claim 1.

9. The method of claim 8, where said fungi are false mildews.

* * * * *